United States Patent [19]
Bennett et al.

[11] Patent Number: 5,516,784
[45] Date of Patent: May 14, 1996

[54] ANTI-HIV (AIDS) AGENTS

[75] Inventors: Frank Bennett, Montclair; Ashit Ganguly, Upper Montclair; Viyyoor Girijavallabhan, Parsippany; Naginbhai Patel, Piscataway, all of N.J.

[73] Assignee: Schering Corporation

[21] Appl. No.: 193,161

[22] PCT Filed: Feb. 15, 1992

[86] PCT No.: PCT/US92/06525
§ 371 Date: Feb. 10, 1994
§ 102(e) Date: Feb. 10, 1994

[87] PCT Pub. No.: WO93/04043
PCT Pub. Date: Mar. 4, 1993

[51] Int. Cl.$^6$ .................. A61K 31/47; A61K 31/44; A61K 31/495; A61K 31/425; C07D 215/48; C07D 241/36; C07D 471/04; C07D 475/00

[52] U.S. Cl. .......... 514/311; 514/235.2; 514/248; 514/249; 514/258; 514/274; 514/300; 514/345; 514/355; 514/357; 514/365; 514/383; 514/399; 514/419; 514/453; 514/602; 514/616; 544/128; 544/235; 544/316; 544/354; 544/355; 546/122; 546/169; 546/298; 546/316; 546/323; 548/202; 548/267.8; 548/338.1; 548/516; 549/405; 560/27; 564/80; 564/153

[58] Field of Search ............ 546/174, 323, 546/122, 169, 298, 316; 514/235.2, 248, 249, 258, 274, 300, 311, 345, 355, 365, 383, 399, 419, 453, 602, 616; 544/128, 235, 316, 354, 355; 548/202, 267.8, 338.1, 516; 549/405; 560/27; 564/80, 153

[56] References Cited

U.S. PATENT DOCUMENTS 5,256,677 10/1993 Sham ....................... 514/351

FOREIGN PATENT DOCUMENTS

| | | |
|---|---|---|
| 0270234 | 6/1988 | European Pat. Off. . |
| 0310918 | 4/1989 | European Pat. Off. . |
| 0346847 | 12/1989 | European Pat. Off. . |
| 0386611 | 9/1990 | European Pat. Off. . |
| 0399556 | 11/1990 | European Pat. Off. . |
| 0401676 | 12/1990 | European Pat. Off. . |
| 0431520 | 6/1991 | European Pat. Off. . |

OTHER PUBLICATIONS

Debouck, C. AIDS Res. Hum. Retrov., 1992 8(2) 153–164 (Original article is an order).
Roberts, N. A. et al. Science 1990, 248, 358–361 (Parent application 1449–AR).
March, J. 'Advanced Organic Chemistry. Reactions, Mechanisms, and Structure' McGraw Hill, 1977. p. 360.
Yarchoan, R. and Broder S. 1992 J. Enzyme Inhibition 6, 99–111.
Science, vol. 248, pp. 358–361, Roberts et al, Rational Design of Peptide–Based HIV Proteinase Inhibitors (Apr., 1990).
Journal of Cellular Biochemistry, Keystone Symposia on Molecular and Cellular Biology (1994) Abstract S039.
J. Org. Chem., vol. 59, p. 3656 1994 Parks et al.

*Primary Examiner*—C. Warren Ivy
*Assistant Examiner*—Evelyn Huang
*Attorney, Agent, or Firm*—Matthew Boxer

[57] ABSTRACT

Compounds of formula $$Ar\underset{W}{\diagdown}\underset{|}{\overset{Z}{N}}\underset{Q}{\diagdown}\underset{\|}{\overset{O}{C}}\underset{H}{\diagdown}\underset{|}{\overset{R_1}{N}}\underset{U}{\diagdown}T$$

wherein Ar, W, Z, Q, $R_1$, U, and T are as set forth herein, are described. These compounds are active as agents against retroviruses and in particular against HIV.

18 Claims, No Drawings

ANTI-HIV (AIDS) AGENTS
SUMMARY OF THE INVENTION
This application is the national phase of PCT/US92/06525 filed on Aug. 11, 1992.
The invention relates to compounds of the formula
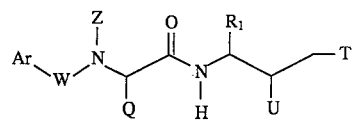
or a pharmaceutically acceptable salt thereof, wherein Ar is
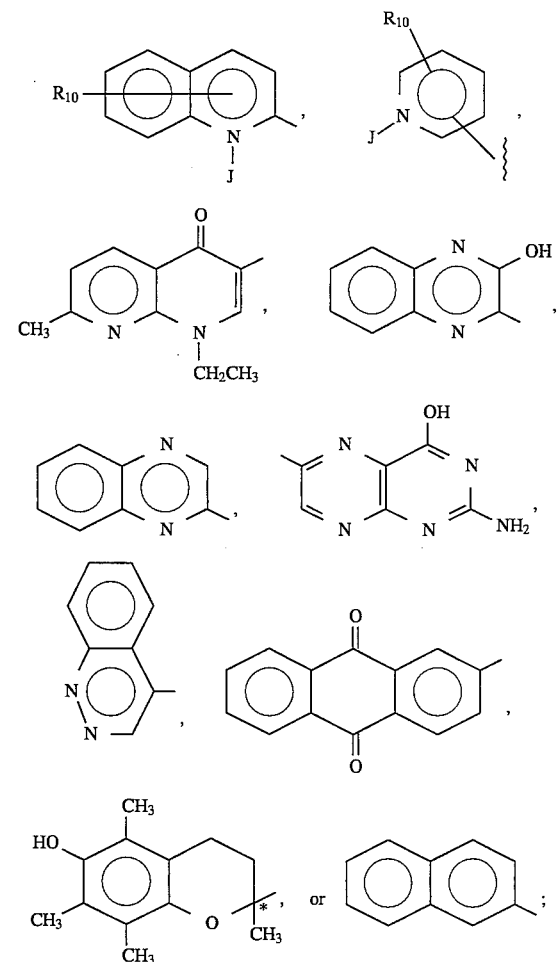
*denotes a mixture of isomers
$R_{10}$ is H or OH;
J is O or an electron pair;
W is
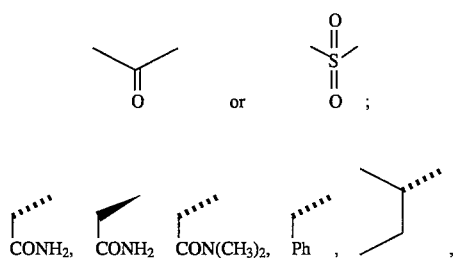
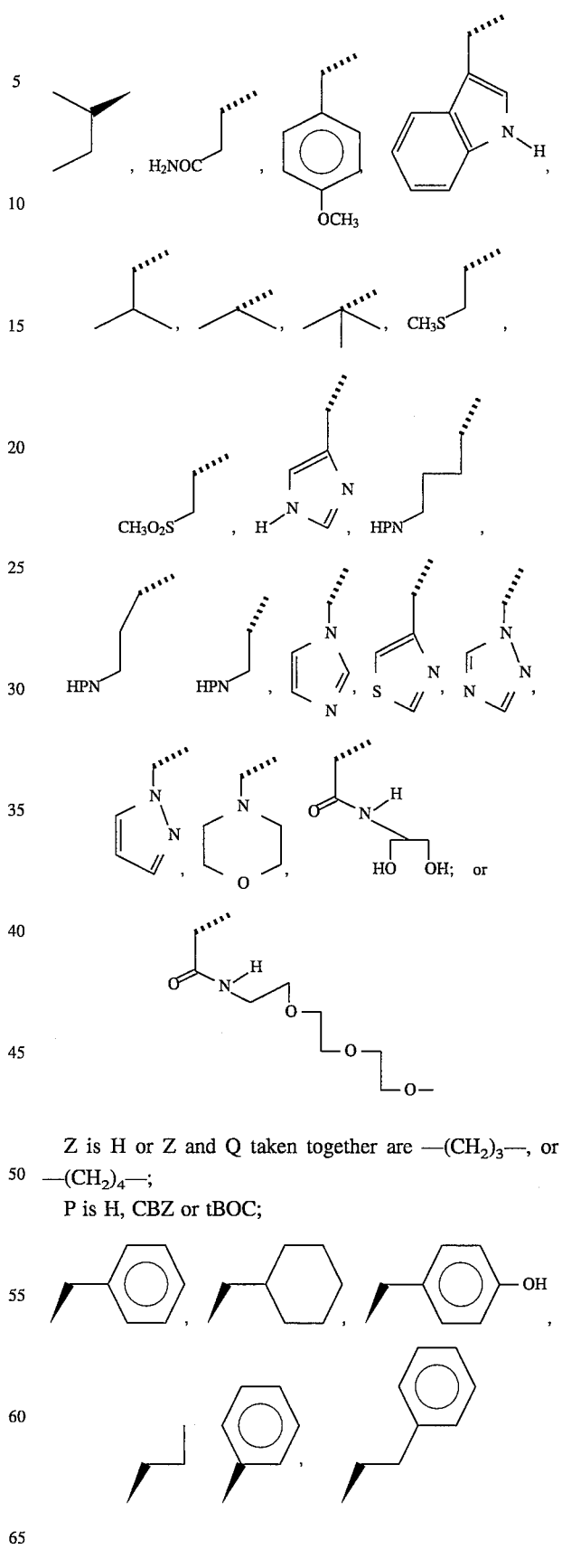
Z is H or Z and Q taken together are —$(CH_2)_3$—, or —$(CH_2)_4$—;
P is H, CBZ or tBOC;

HO''', HO'; [carbamate structures with NH2]

T is —Y—L wherein
wherein Y is —SO—, —SC$_2$—, S, or O
L is

[phenyl-COR$_2$], [cyclohexyl-COR$_2$], [cyclopentyl-COR$_2$],

[naphthyl-COR$_2$], [pyridyl-COR$_2$],

[pyridyl-COR$_2$], [benzimidazolyl],

[quinoxalinyl with C(O)R$_2$],   or   —(CH$_2$)$_q$—COR$_2$;

—O—C$_1$-C$_{12}$ alkyl,   —O—(CH$_2$)$_m$Ph,   —N(H)—C$_1$-C$_{12}$ alkyl,

—N(H)—(CH$_2$)$_p$Ph,   —N(H)—C$_3$-C$_{10}$ cyclic alkyl,   —N(H)—CH(CH$_2$OH)$_2$, —N(H)—CH$_2$CH$_2$—O—CH$_2$CH$_2$—O—CH$_3$,   —N(piperidinyl), —N(morpholinyl) O,   or   —N(pyrrolidinyl);

m is 0, 1 or 2;
p is 0, 1, or 2; and
q is 0, 1, or 2; or an isomer thereof.
Preferred are compounds of formula I wherein Y is S.
Preferred are compounds of formula I wherein L is [2-(NHtBu-carbonyl)phenyl with O].

Preferred are compounds of formula I wherein Ar is

[quinoline with R$_{10}$ and N-J, 2-substituted].

Preferred among such compounds are those wherein Ar is

[quinolin-2-yl], [6-HO-quinolin-2-yl],

[quinoline N-oxide, 2-yl],   or   [4-OH-quinolin-2-yl].

Especially preferred among such compounds are those compounds of formula I wherein Ar is

[quinolin-2-yl].

Also preferred are compounds of formula I wherein Ar is

[pyridine with R$_{10}$ and N-J].

Preferred among such compounds are those wherein Ar is

[pyridin-2-yl], [pyridine N-oxide, 2-yl], [HO-pyridin-2-yl],

[pyridine N-oxide], or [HO-pyridin-yl].

Preferred are compounds of formula I wherein W is CO.
Preferred are compounds of formula I wherein Z is H.
Preferred are compounds of formula I wherein Q is

[CH''' with CONH$_2$].

Preferred are compounds of formula I wherein R$_1$ is

[CH with Ph].

Preferred are compounds of formula I wherein U is

Preferred are compounds of formula I wherein J is an electron pair.

Preferred are compounds of formula I wherein L is

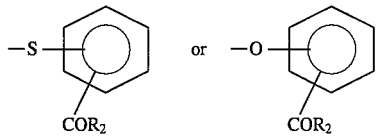

and $R_2$ is —NH tBu or —NHPh.

Most preferred are those compounds as described just above wherein $R_2$ is NH tBu.

As used herein substituted phenyl (as in substituted NHPh) denotes phenyl substituted with up to 5 substituents selected from the group consisting of alkyl, alkoxy, halogen, $NH_2$, OH, $NO_2$, CN, S-alkyl, —$SO_2$-alkyl, —CO-alkyl, COOH, COOalkyl, naphthalene, substituted naphthalene, quinoline, and substituted quinoline but no more than three of the same substituent on a given phenyl ring.

Substituted naphthalene denotes naphthalene substituted with up to 7 substituents selected from the group consisting of alkyl, alkoxy, halogen, $NH_2$, OH, $NO_2$, CN, S-alkyl, —$SO_2$-alkyl, —CO-alkyl, COOH, COOalkyl, but no more than four of the same substituent on a given naphthalene ring.

Substituted quinoline denotes quinoline substituted with up to 6 substituents selected from the group consisting of alkyl, alkoxy, halogen, $NH_2$, OH, $NO_2$, CN, S-alkyl, —$SO_2$-alkyl, —CO-alkyl, COOH, COOalkyl, but no more than four of the same substituent on a given quinoline ring.

Alkyl denotes straight or branched saturated hydrocarbons which contain from 1 to 12 carbon atoms. Representative examples include methyl, butyl, isobutyl, isoamyl, and the like. Alternatively, the number of carbon atoms in a particular alkyl may be specified. For example, $C_1$-$C_7$ alkyl refers to an alkyl which may have one to seven carbon atoms.

Alkoxy denotes —O-alkyl wherein alkyl is as described above.

Cyclic alkyl denotes a cyclic alkyl having from 3 to 10 carbon atoms and which may optionally have one or more fused or bridged rings.

Ph denotes phenyl.

Halogen denotes chlorine, fluorine or bromine.

As used herein, a boldfaced line denotes a bond that comes up above the plane of the page. A dashed line denotes a bond that goes down below the plane of the page. A wavy line denotes either racemic mixture or that the stereochemistry of this bond is not known.

Exemplary compounds of the invention include:

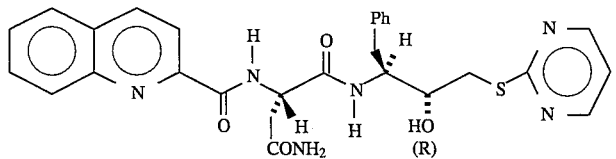

1.

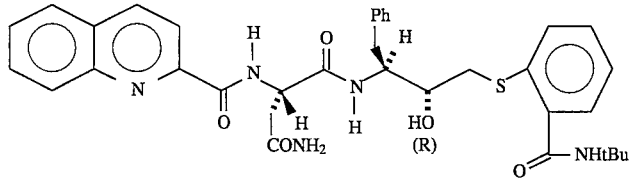

2.

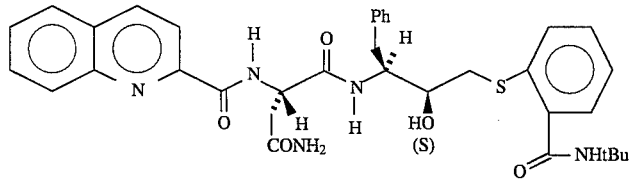

3.

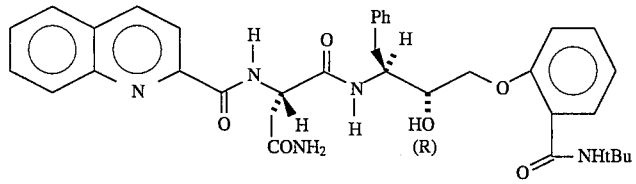

4.

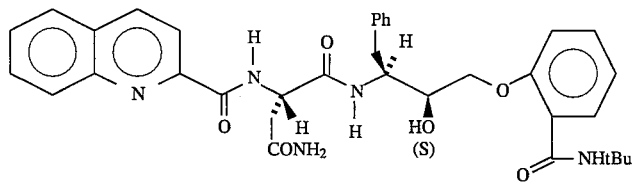

5.

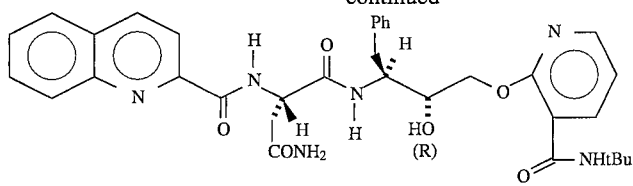
6.
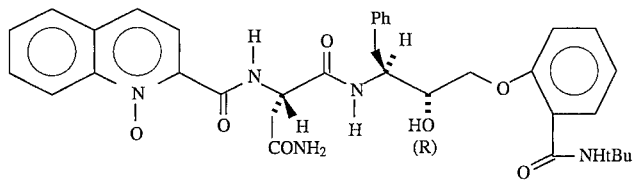
7.
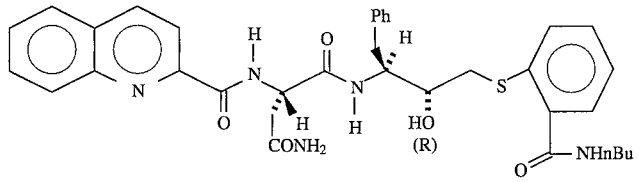
8.
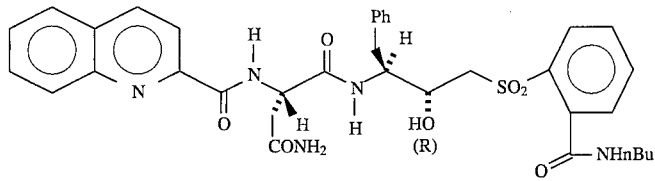
9.
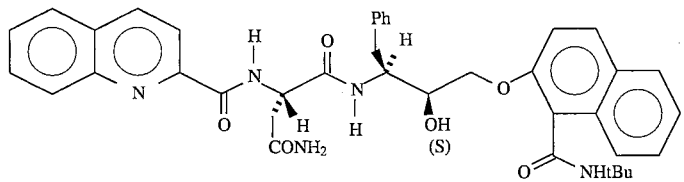
10.
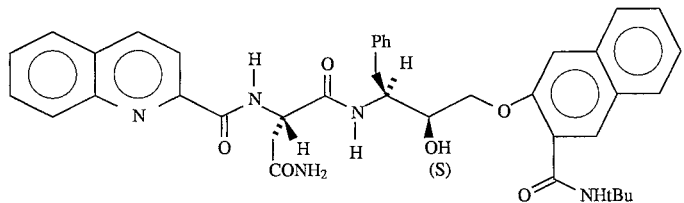
11.
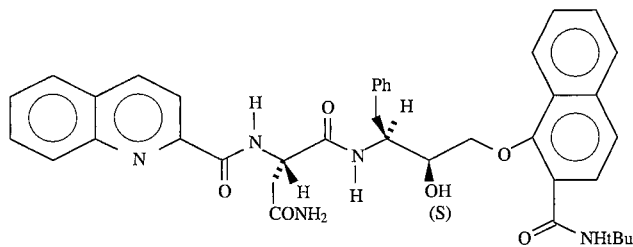
12.
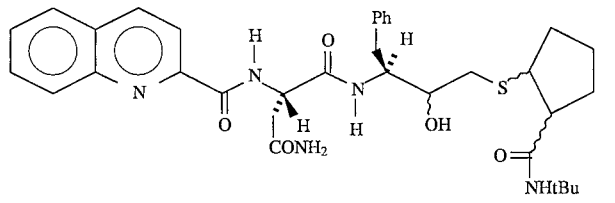
13.

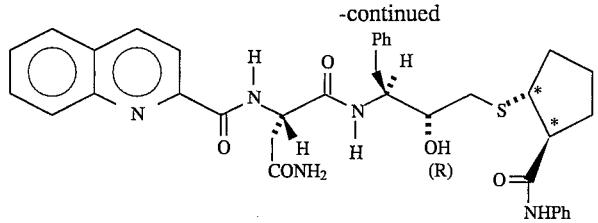
as used here and below, * means that the relative stereochemistry of the two chiral centers is known, but the absolute stereochemistry is not known
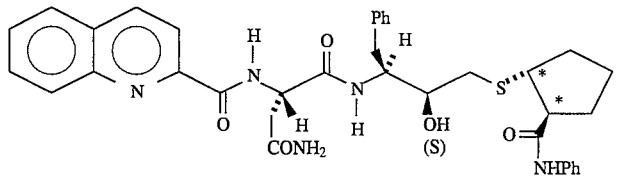
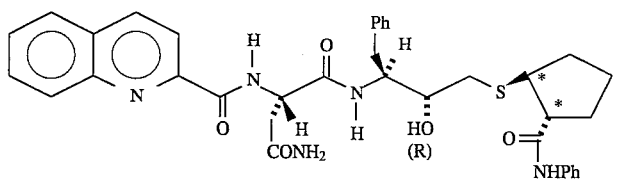
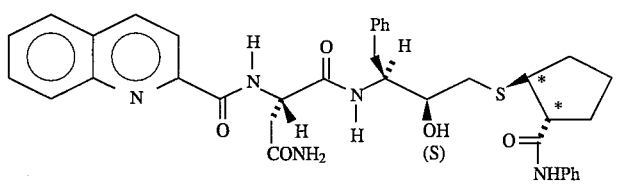
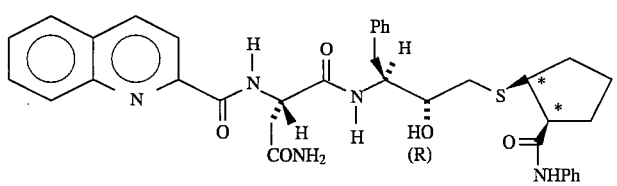
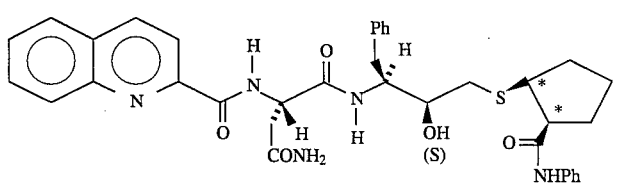
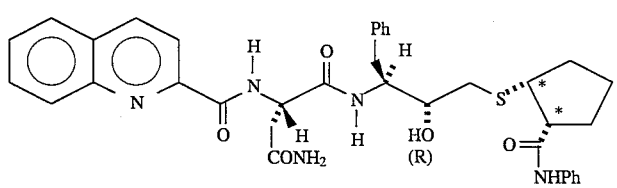
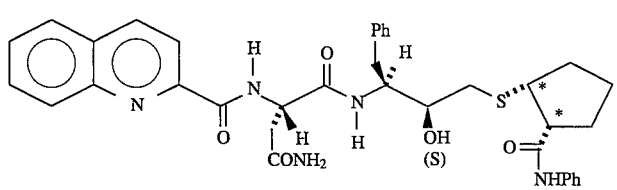

-continued
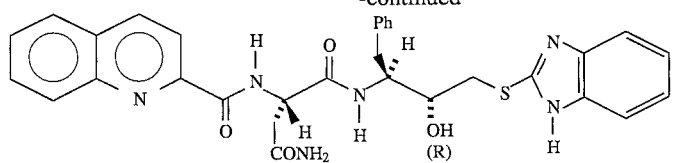 22.
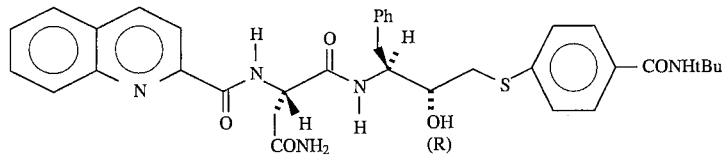 23.
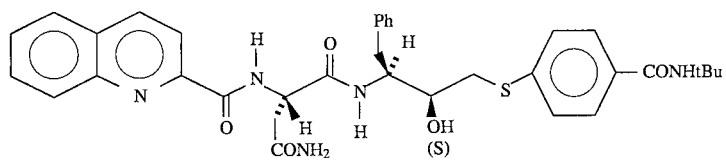 24.
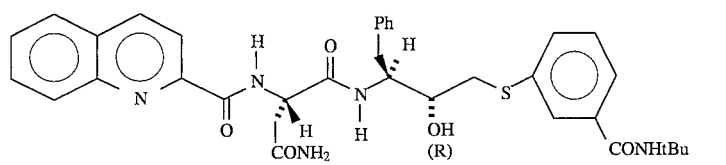 25.
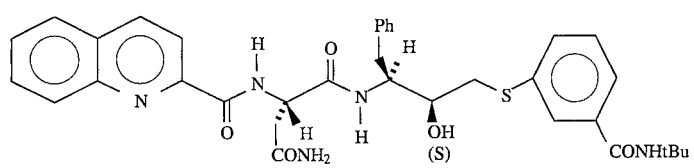 26.
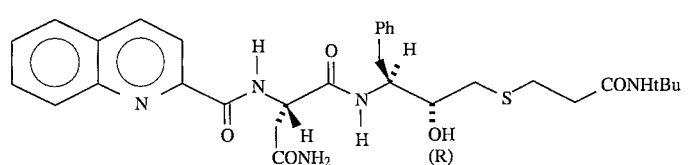 27.
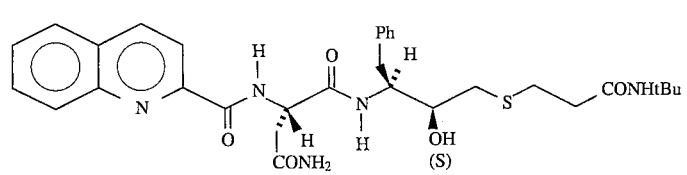 28.
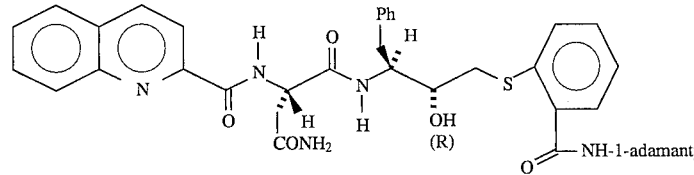 29.
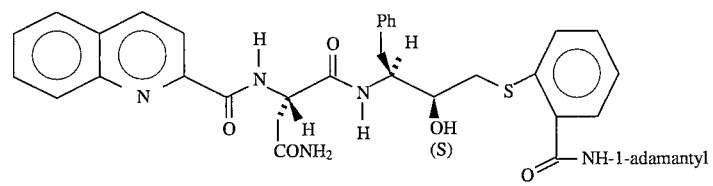 30.

-continued
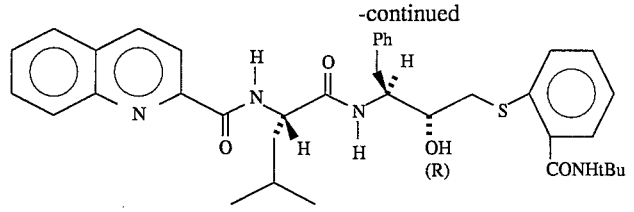 31.
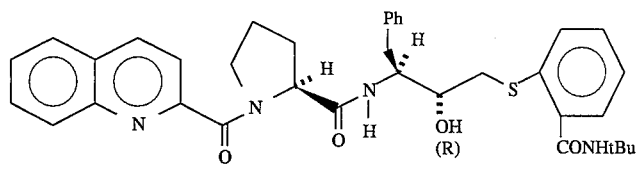 32.
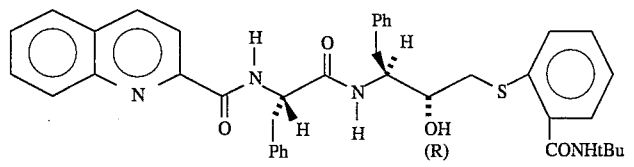 33.
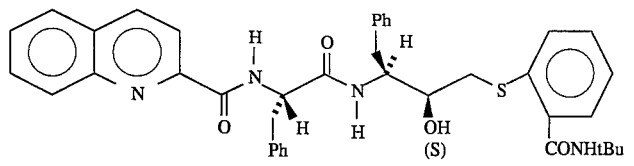 34.
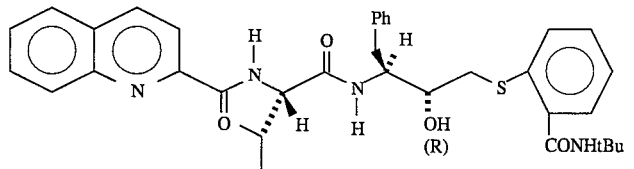 35.
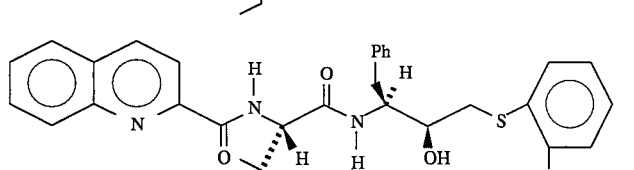 36.
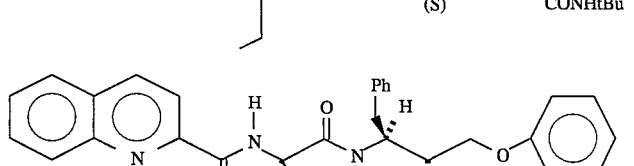 37.
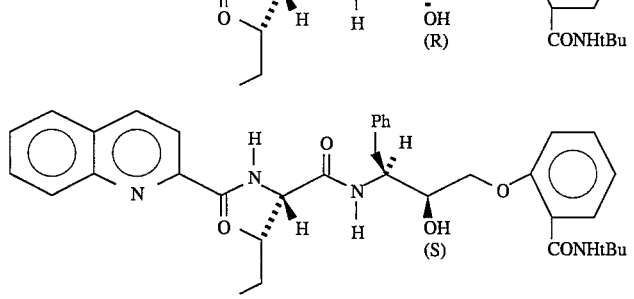 38.

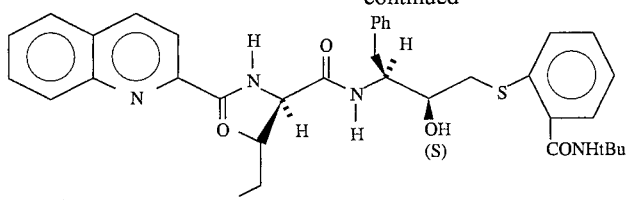
39.
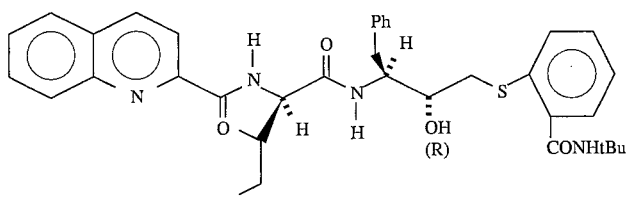
40.
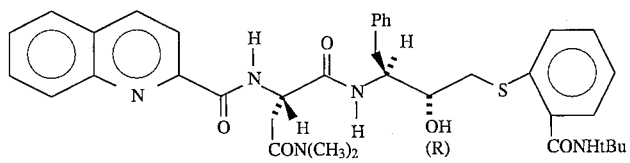
41.
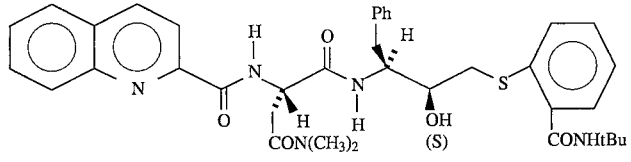
42.
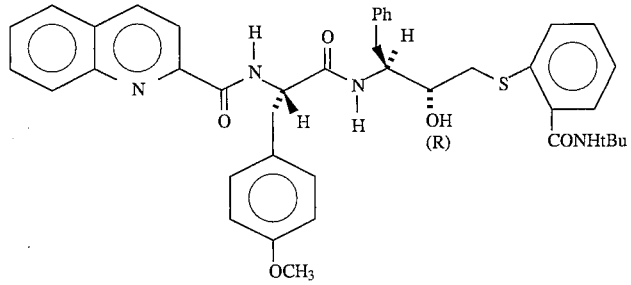
43.
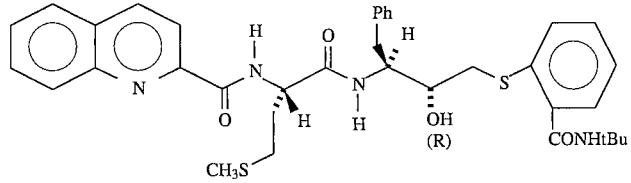
44.
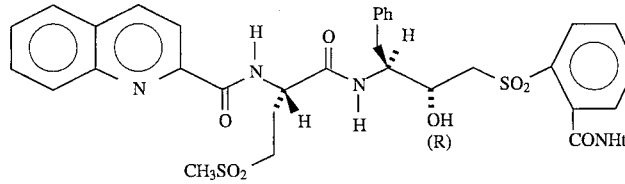
45.
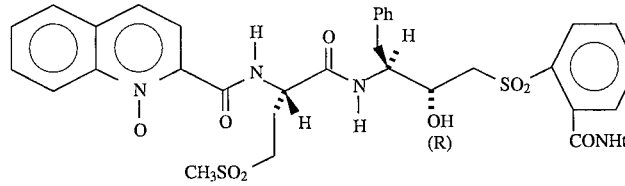
46.

-continued
47. 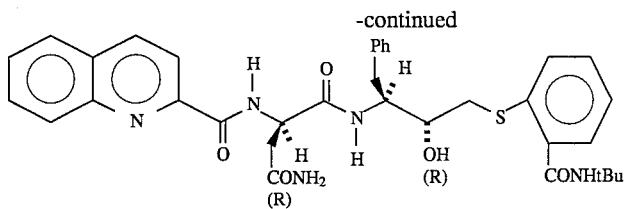
48. 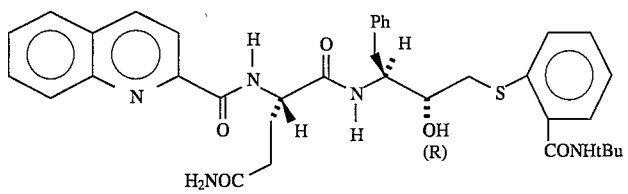
49. 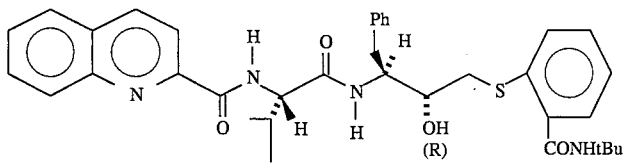
50. 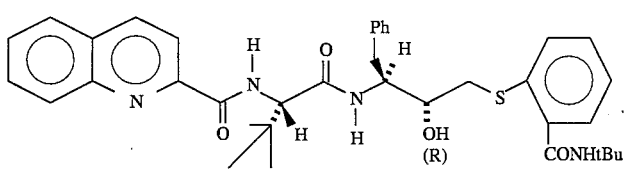
51. 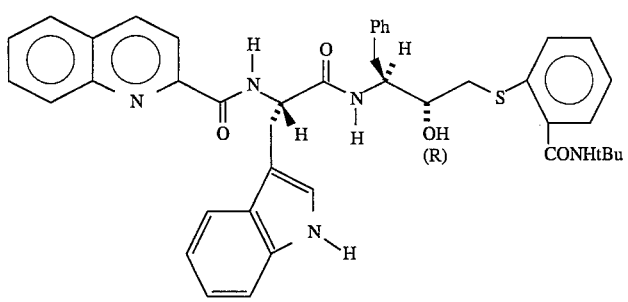
52. 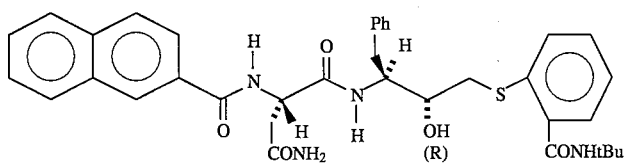
53. 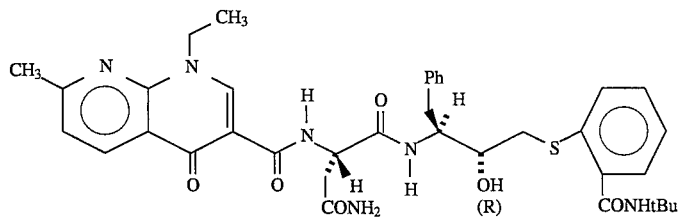
54. 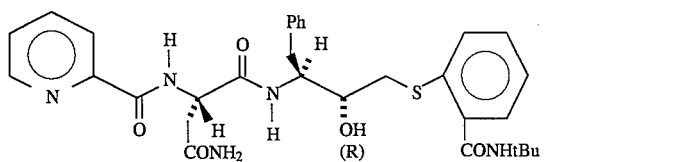

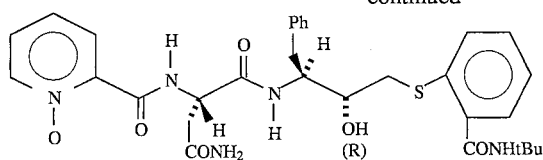
55.
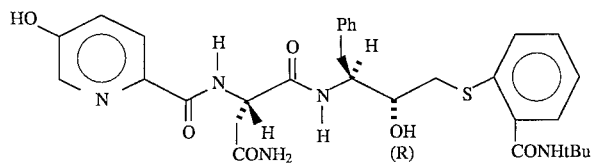
56.
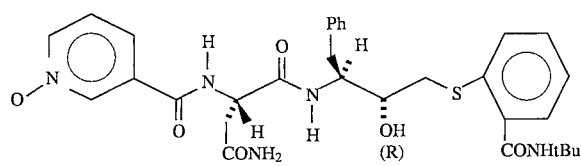
57.
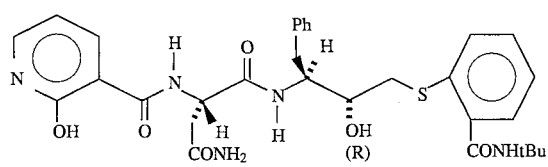
58.
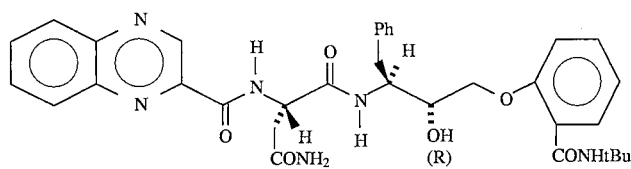
59.
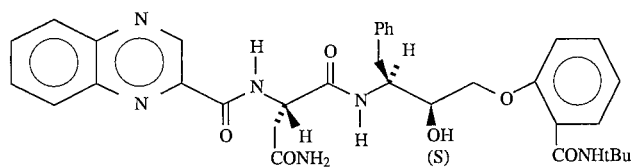
60.
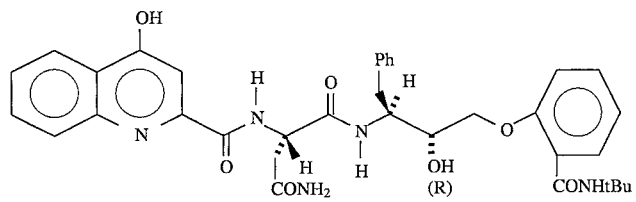
61.
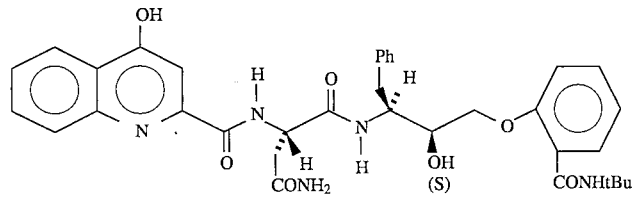
62.
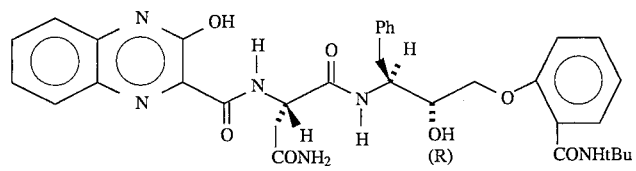
63.

64. 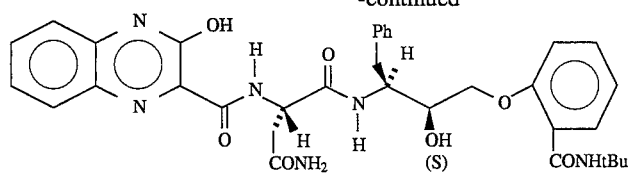
65. 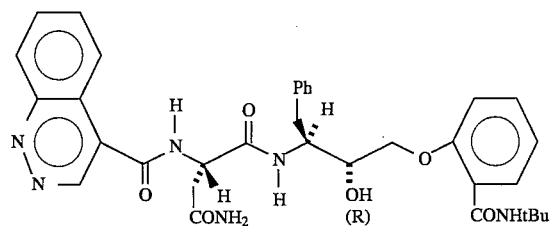
66. 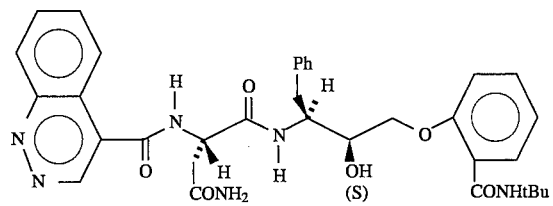
67. 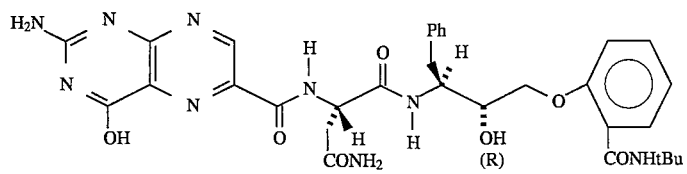
68. 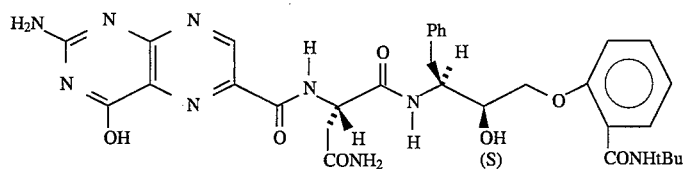
69. 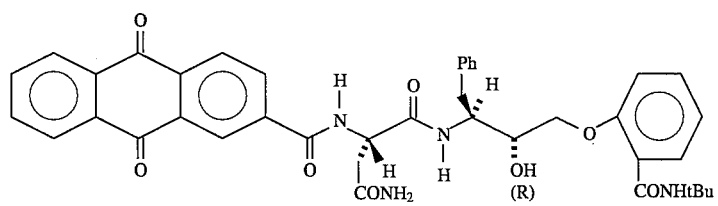
70. 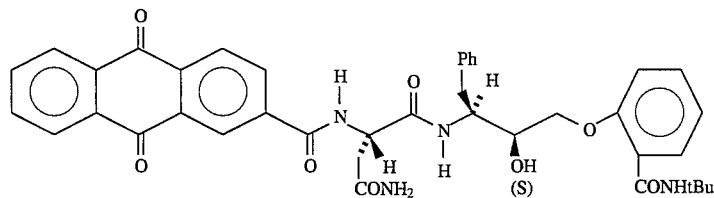
71. 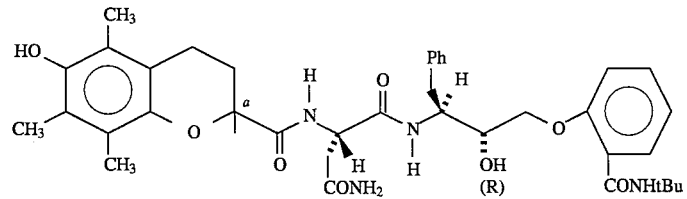
a = a mixture of isomers at this chiral center 72. 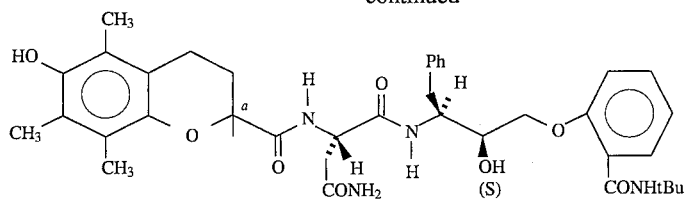
a = a mixture of isomers at this chiral center
73. 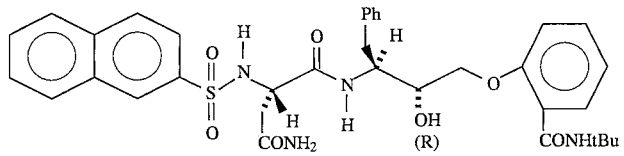
74. 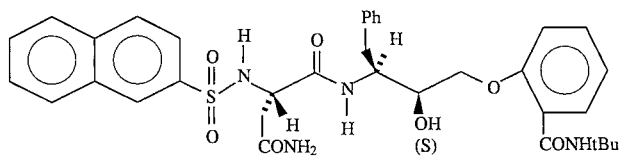
75. 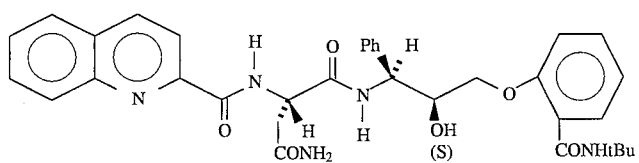
76. 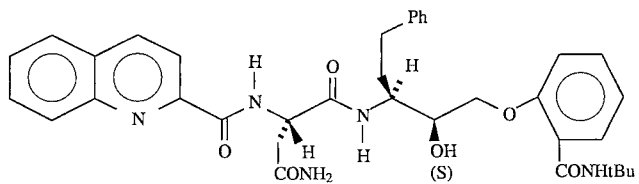
77. 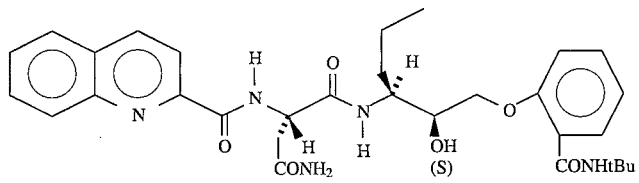
78. 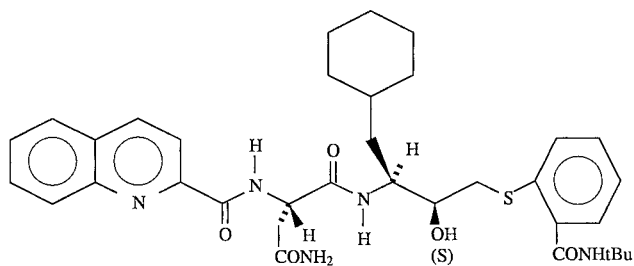
79. 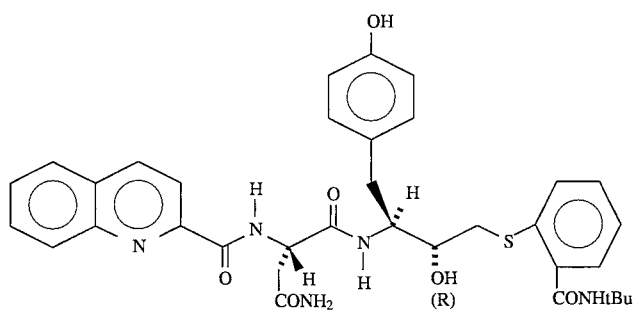

-continued
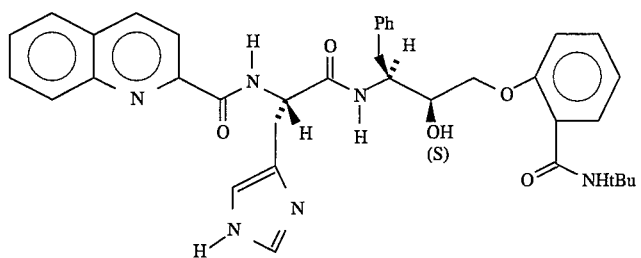 80.
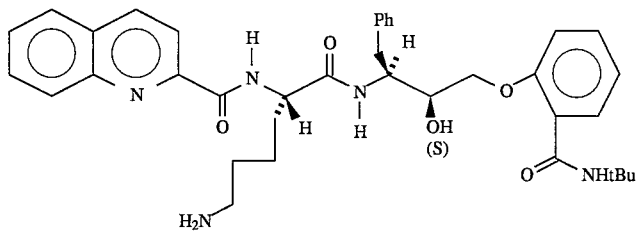 81.
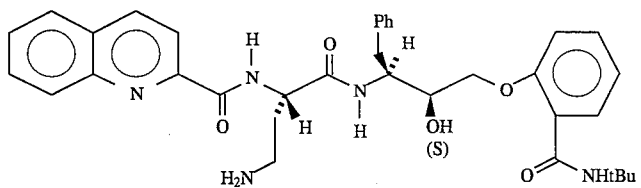 82.
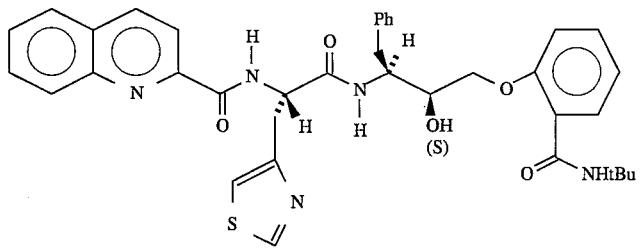 83.
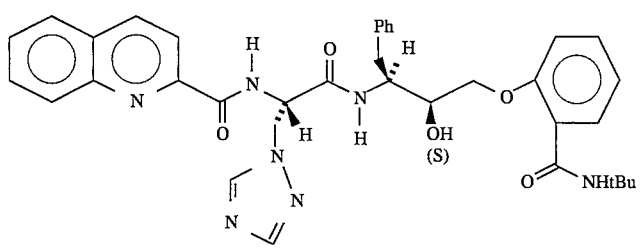 84.
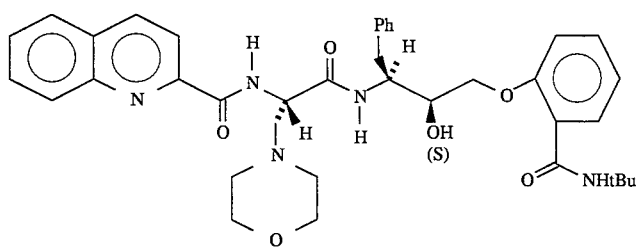 85.

-continued
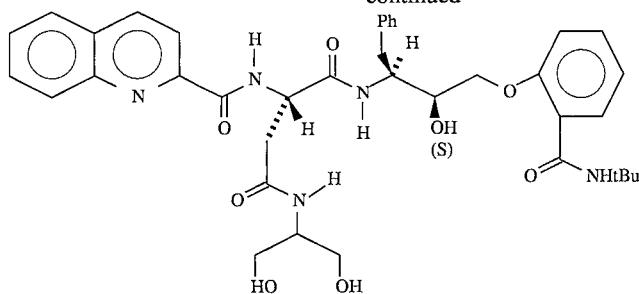
86.
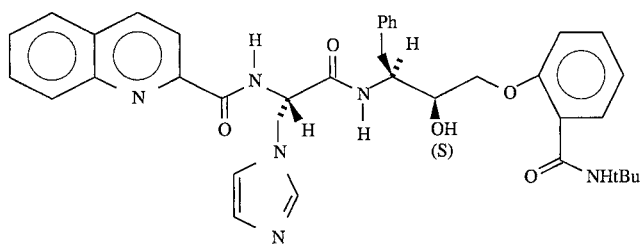
87.
As used herein, tBu means tert.-butyl and nBu means normal-butyl.
Preferred compounds of the invention are:
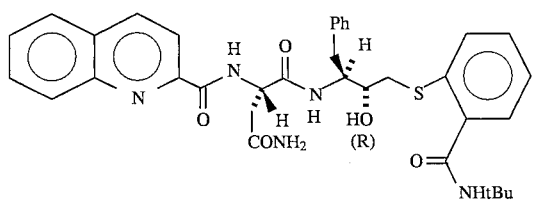
30
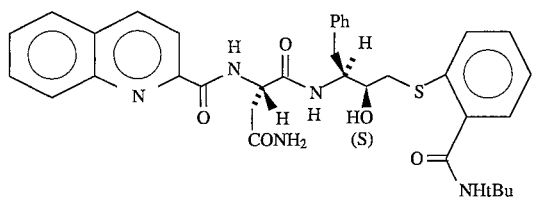
40
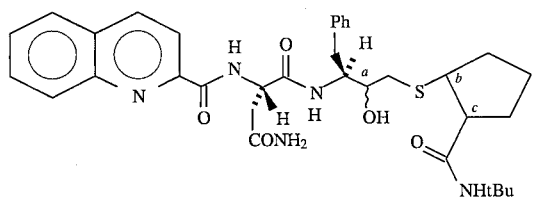
wherein all possible epimers are present at the carbons labelled a, b, and c
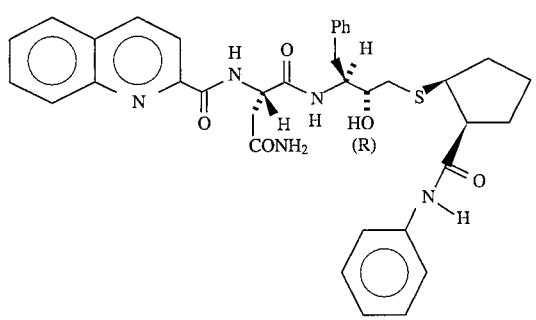
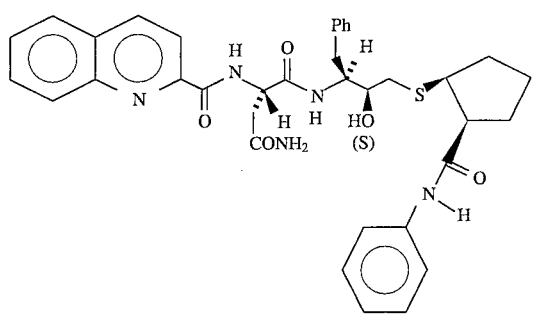
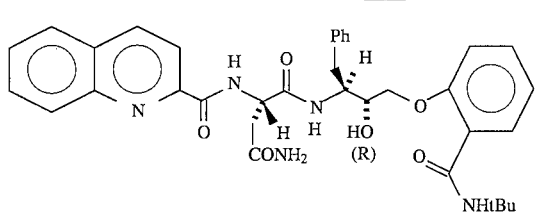
and

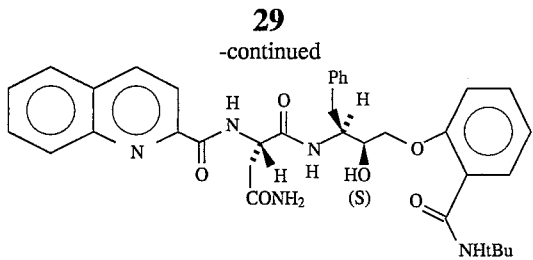

The most preferred compound of the invention is:

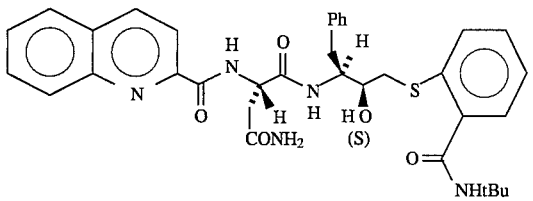

The chemical name for this compound is: N-(1,1-Dimethyl ethyl)-2-[[[3-[N-(2-quinolinylcarbonyl)-L-asparaginyl]amino]- 3(S)-phenylmethyl-2(S)-hydroxy propyl]thio]-benzamide.

The invention also relates to a pharmaceutical composition which comprises a compound of formula I in combination with a pharmaceutically acceptable carrier material.

The invention also relates to a method for treating AIDS which comprises administering to a patient in need of such treatment an anti-HIV effective amount of a compound of formula I.

As pointed out herein, compounds of formula VI are also active against retroviruses including HIV; and are also active against renin synthesis and are therefore believed to active against hypertension. Examples of compounds of formula VI, which are intermediates in the preparation of compounds of formula I, are set forth just below. The numbering for these intermediate compounds is the same as that used in the table below. In the table below, "IN 1", for example means intermediate 1. Physical data are also given for each of the intermediate compounds below. These intermediate compounds may be prepared in accordance with the Formula Schemes and reaction descriptions set forth herein.

INTERMEDIATE NO. 1

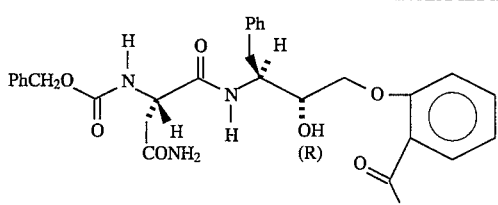

INTERMEDIATE NO. 2

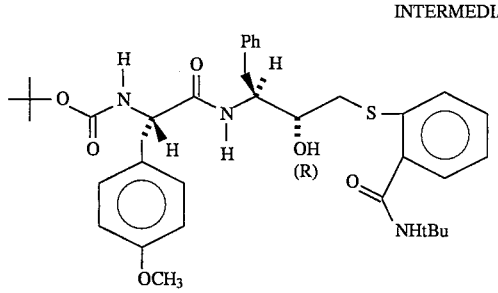

INTERMEDIATE NO. 3

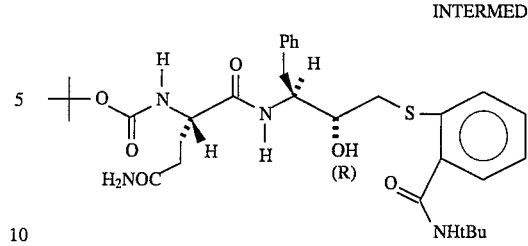

INTERMEDIATE NO. 4

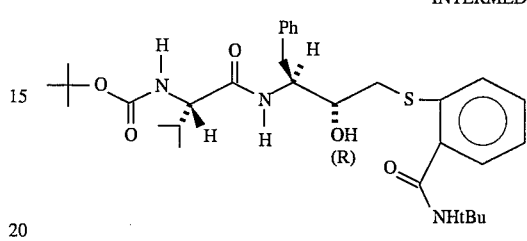

INTERMEDIATE NO. 5

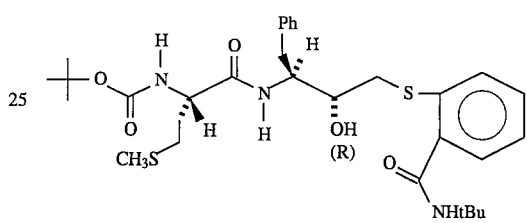

INTERMEDIATE NO. 6

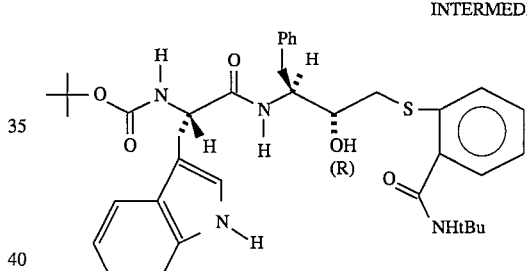

INTERMEDIATE NO. 7

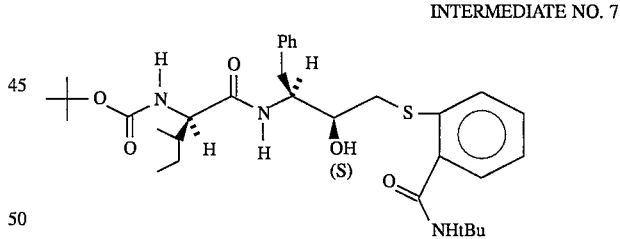

INTERMEDIATE NO. 8

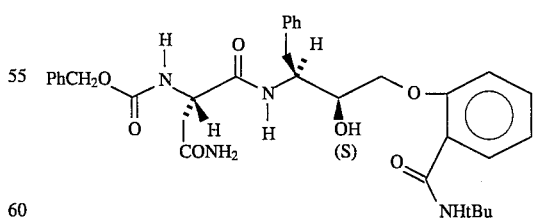

Compounds of formula V are also active against retroviruses including HIV and are also active against renin synthesis and are therefore believed to active against hypertension. Examples of compounds of formula V, which are intermediates in the preparation of compounds of formula I, are set forth below.

DETAILED DESCRIPTION OF THE INVENTION

Asymmetric centers exist in compounds of formula I of the invention. Accordingly, such compounds of formulas I include stereoisomers.

All such isomeric forms and mixtures thereof are within the scope of the present invention. Unless otherwise indicated, the methods of preparation may result in product distributions which include all possible structural isomers, although it is understood that physiological response may vary according to stereochemical structure. The isomers may be separated by conventional means such as fractional crystallization or HPLC (high performance liquid chromatography).

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

The compounds of formulas I form pharmaceutically acceptable salts. The preferred pharmaceutically acceptable salts are nontoxic, acid addition salts formed by adding to a compound of the invention about a stoichiometic amount of a mineral acid such as HCl, HBr, $H_2SO_4$, or $H_3PO_4$ or of an organic acid such as acetic acid, propionic, valeric, oleic, palmitic, stearic, lauric, benzoic, lactic, paratoluenesulfonic, methane sulfonic, citric, maleic, fumaric, succinic and the like, respectively.

The compounds of formulas I' may be prepared by the methods described below with reference to the Scheme 1.

FORMULA SCHEME 1

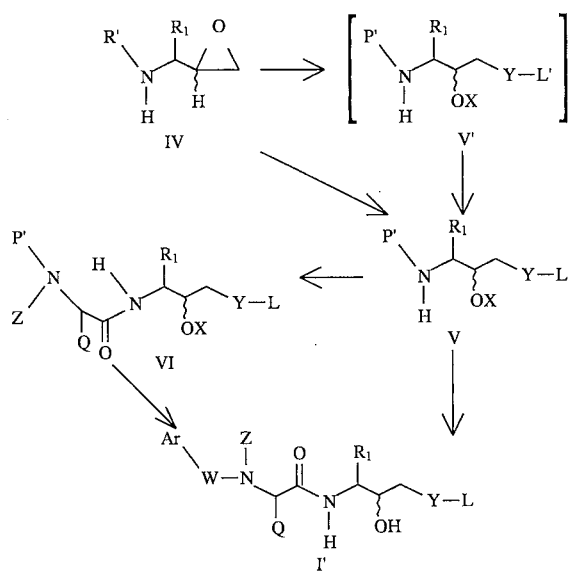

wherein X is H or a negative charge,

Y and L are as described above, L' corresponds to L except that $R_2$ is OH.

P' is a conventional nitrogen-protecting group such as t-butoxycarbonyl (BOC) or benzyloxycarbonyl (CBZ), or H is

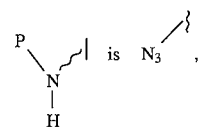

that is azide, and brackets [] denote a compound which was formed but not isolated during the synthesis.

The compounds of formula IV are known, can be prepared in accordance with known methods, or else their preparation is described herein. For example, compounds of formula IV, including particular stereoisimers thereof, may be made by methods analogous to those set forth in *Drugs of the Future*, 1991, 16(3):210–212, and Ghosh et al, *J Chem Soc Chem Commun* 1992, P. 273 which are herein incorporated by reference.

Where Y is S, a compound of formula IV may be converted to a compound of formula V' by reaction with a thiolate in an organic solvent such as methanol, dimethylsulfoxide (DMSO), or more preferably ethanol at a temperature in the range of about 0° to about 80°, more preferably 25°. The resulting compound of formula V' may be isolated by conventional means such as crystallization or chromatography or it may be used directly in the next step of a synthesis of this invention to form a compound of formula V.

Also, where Y is S, compound of formula IV may be converted to a compound of formula V by reaction with a thiolate in an organic solvent such as DMSO, methanol or more preferably ethanol at a temperature in the range of about 0° to about 80°, more preferably 25°. The resulting compound of formula V may be isolated by conventional means such as crystallization or chromatography or it may be used directly in the next step of a synthesis of this invention.

When Y is O, compound of formula IV must be converted directly to a compound of formula V by reaction with an alcohol (XYL is HO-L) in an organic solvent such as DMSO, or more preferably DMF at a temperature in the range of about 100° to about 150°, more preferably 120°. This reaction may be catalyzed by acids or silica gel. The resulting compound of formula V may be isolated by conventional means such as crystallization or chromatography or it may be used directly in the next step of a synthesis of this invention.

A compound of formula V may be converted to a compound of formula I' by first removing the protecting group P which can be t-butoxy carbonyl (BOC), benzyloxycarbonyl (CBZ) or azide. In the case of BOC, removal is carried out in a solvent such as $CHCl_3$ or $CH_2Cl_2$ at a temperature in the range of about 0° to about 25° in the presence of trifluoroacetic acid. In the case of CBZ, removal is carried out in the presence of a hydrogenation catalyst such as 10% Pd/C and in a solvent such as methanol or ethanol at a temperature in the range of about 25° to about 35°. The reaction is carried out under one atmosphere of hydrogen. Where

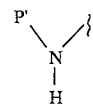

is azide, the azide may be converted to its corresponding amine in the presence of a hydrogenation catalyst such as 10% Pd/C and in a solvent such as methanol or ethanol at a temperature in the range of about 25° to about 35° C. The reaction is carried out under one atmosphere of hydrogen.

This reaction is followed by reacting the deprotected amine with an active ester or mixed anhydride of

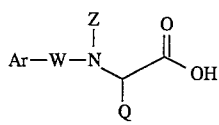

in an appropriate solvent, preferably CHCl₃ or CH₂Cl₂. (The active ester or the mixed anhydride of

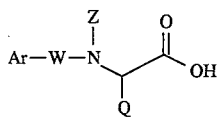

is made by reacting the acid with benzotriazol-1-yloxytris(dimethylamino)phosphonium hexafluorophosphate (BOP)in an organic solvent, preferably CHCl₃ or CH₂Cl₂ in the presence of an acid scavenger such as triethylamine. The mixed anhydride of

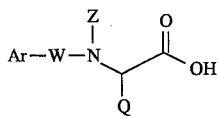

can be made by conventional means, preferably as pivaloyl mixed anhydride

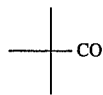

using pivaloyl chloride in an organic solvent like CH₂Cl₂ in the presence of a base such as triethylamine at 0° to –60° C.)

The resulting compound of formula I' may be isolated by conventional means such as crystallization or chromatography.

Alternatively, a compound of formula I' may be obtained from a compound of formula V via an intermediate of formula VI.

A compound of formula V may be converted to a compound of formula VI by first removing the protecting group P which can be t-butoxy carbonyl (BOC) or benzyloxycarbonyl (CBZ) or azide. In the case of BOC, removal is carried out in a solvent such as CHCl₃ or CH₂Cl₂ at a temperature in the range of about 0° to about 25° in the presence of trifluoroacetic acid. In the case of CBZ, removal is carried out with a hydrogenation catalyst as described above, in a solvent such as methanol or ethanol a temperature in the range of about 25° to about 35°. The reaction is carried out under one atmosphere of hydrogen. Where

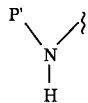

is azide, the azide may be converted to its corresponding amine with a hydrogenation catalyst as described above, in a solvent such as methanol or ethanol at a temperature in the range of about 25° to about 35° C. The reaction is carded out under one atmosphere of hydrogen. This reaction is followed by reacting the deprotected amine with an active ester or mixed anhydride of

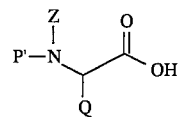

in an appropriate solvent, preferably CHCl₃ or CH₂Cl₂. (The active ester or the mixed anhydride of

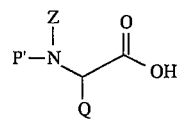

is made by reacting the acid with benzotriazol-1-yloxytris(dimethylamino)phosphonium hexafluorophosphate (BOP)in an organic solvent, preferably CHCl₃ or CH₂Cl₂ in the presence of an acid scavenger such as triethylamine. The mixed anhydride of

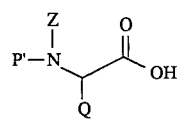

can be made by conventional means, preferably as pivaloyl mixed anhydride

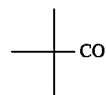

using pivaloyl chloride in an organic solvent like CH₂Cl₂ in the presence of a base such as triethylamine at 0° to –60° C.)

The resulting compound of formula VI may be isolated by conventional means such as crystallization or chromatography.

A compound of formula VI may be converted to a compound of formula I' by first removing the protecting group P which can be t-butoxy carbonyl (BOC) or benzyloxycarbonyl (CBZ). In the case of BOC, removal is carried out in a solvent such as CHCl₃ or CH₂Cl₂ at a temperature in the range of about 0° to about 25° in the presence of trifluoroacetic acid. In the case of CBZ, removal is carried out with a hydrogenation catalyst as described above, in a solvent such as methanol or ethanol a temperature in the range of about 25° to about 35°. The reaction is carried out under one atmosphere of hydrogen. Where

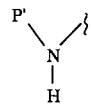

is azide, the azide may be converted to its corresponding amine with a hydrogenation catalyst as described above, in a solvent such as methanol or ethanol at a temperature in the range of about 25° to about 35° C. The reaction is carried out under one atmosphere of hydrogen. This reaction is followed by reacting the deprotected amine with an active ester or mixed anhydride or acid chloride of ArCO₂H or ArSO₃H in an appropriate solvent, preferably CHCl₃ or CH₂Cl₂ in the presence of an amine base such as triethylamine.

(The active ester or the mixed anhydride of ArCO₂H or ArSO₃H is made by reacting the acid with benzotriazol-1-yloxytris(dimethylamino)phosphonium hexafluorophosphate (BOP)in an organic solvent, preferably CHCl₃ or CH$_2$Cl$_2$ in the presence of an acid scavenger such as triethylamine. The mixed anhydride of ArCO$_2$H or ArSO$_3$H can be made by conventional means, preferably as pivaloyl mixed anhydride

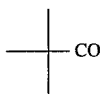

using pivaloyl chloride in an organic solvent like CH$_2$Cl$_2$ in the presence of a base such as triethylamine at 0° to −60° C.)

The resulting compound of formula I' may be isolated by conventional means such as crystallization or chromatography.

Because —Y—L is T, it will be appreciated that compounds of formula I' fall within formula I of the invention.

While Formula Scheme 1 has been drawn using formulas that do not show stereochemistry for OH in the right hand moiety

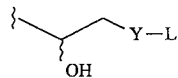

of the compounds, it will be understood that compounds with a specific stereochemistry on the OH bearing carbon can be made.

For example, plate chromatography of a compound of formula

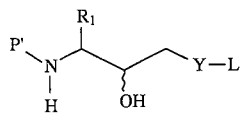

can be used to isolate a compound of formula

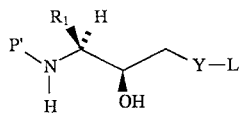

which may in turn be ultimately converted to a compound of formula I with the stereochemistry:

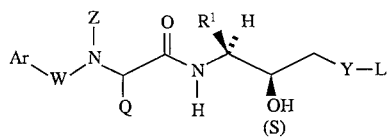

Also ring opening of an epoxide of the formula

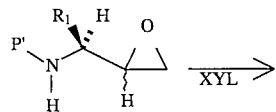

and subsequent acidification and chromatographic separation results in hydroxy compounds of the formulas

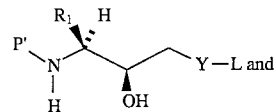

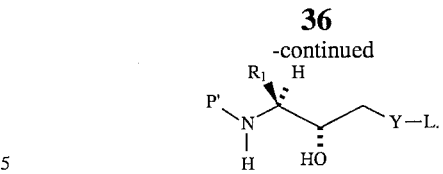

Compounds of formula I wherein Y is S may be converted to corresponding compounds of formula I wherein Y is SO or SO$_2$ by methods analogous to those set forth in the examples below.

Compounds of formula V wherein Y is O, include compounds of formula V" which have the specific alcohol configuration shown. A compound of formula V" may be inverted to its epimer of formula V''' according to Formula Scheme 2 just below.

FORMULA SCHEME 2

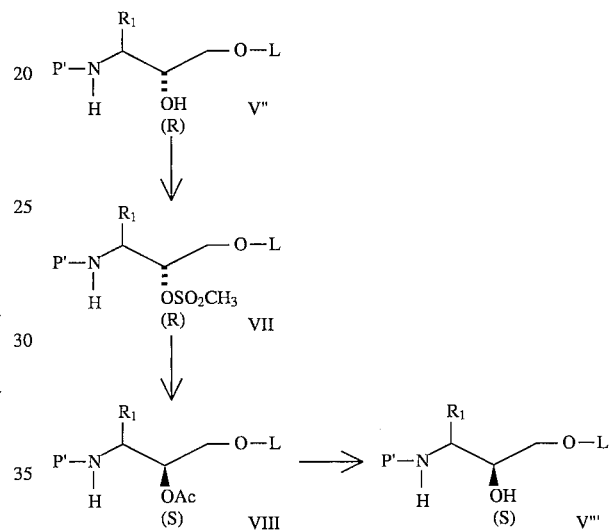

wherein P', R1, and L are as described herein,

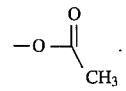

OAc means

A compound of formula V" may be converted to a compound of formula VII by treatment with methane sulfonyl chloride. The reaction is carried out in an organic solvent such as CHCl$_3$ and CH$_2$Cl$_2$ at a temperature in the range of about 0° to about 35° C. in the presence of a base such as Et$_3$N. The resulting compound of formula VII may be isolated by conventional means such as crystallization or chromatography or it may be used in the next step without purification.

A compound of formula VII may be converted to a compound of formula VIII by treatment with cesium acetate. The reaction is carried out in a polar organic solvent such as dimethylformamide (DMF) or dimethylsulfoxide (DMSO) at a temperature in the range of about 50° to about 120° C., preferably 90° under an atmosphere of nitrogen. The resulting compound of formula VIII may be isolated by conventional means such as crystallization or chromatography. A compound of formula VIII may be converted to a compound of formula V''' by treatment with potassium carbonate in a solvent such as methanol or ethanol. The reaction is carried out in a temperature range of about 0° to about 35° C., more preferably 25° C. The resulting compound of formula V''' may be isolated by conventional means such as crystallization or chromatography.

Using the same Formula Scheme 2, a compound of formula V''' may be convened to a compound of formula V''.

Compounds of formula V'' and V''' are encompassed by formula V of Formula Scheme 1. Accordingly, compounds of formula V'' or V''' may be converted to compounds of formula I', having the corresponding stereochemistry for the —OH, by using the chemistry shown in Formula Scheme 1 for converting a compound of formula V to a compound of formula I'.

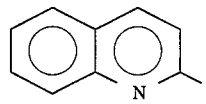

A compound of formula I wherein Ar is for example, may be oxidized by conventional means to obtain a corresponding compound of formula I where Ar is

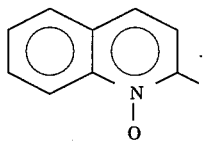

Similarly, a compound of formula I wherein Y is —S— may be oxidized by conventional means to obtain the corresponding compound of formula I where Y is —SO— or —$SO_2$—. Also, sidechains of Q may contain S and these sidechains may be oxidized under the same reaction conditions to —SO— and —$SO_2$—.

The compounds of formula I may also contain protecting groups P which may be removed using the conditions described above, to obtain other compounds of formula I.

The description of the above reactions including oxidations and stereochemical inversions, makes clear that all compounds of formula I of the invention can be synthesized by the chemistry described herein.

The compounds of formula I are active against retroviruses, such HIV, which causes AIDS in humans. Similar retroviruses against which the compounds of formula I are also active include the retrovirus which causes feline AIDS, and the retrovirus which causes Rous' sarcoma which is a disease of chickens.

The compounds of formula I are also expected to be inhibitors of renin synthesis, and as such to be active against hypertension.

The intermediate compounds of formula VI are also active against retroviruses, such HIV, which causes AIDS in humans. Similar retroviruses against which the intermediate compounds of formula VI are also active include the retrovirus which causes feline AIDS, and the retrovirus which causes Rous' sarcoma which is a disease of chickens.

The intermediate compounds of formula VI are also expected to be inhibitors of renin synthesis, and as such to be active against hypertension.

As noted above, the compounds of formula I and VI are active against HIV proteases, including HIV 1.

The compounds of formula I and VI are active as agents for treating AIDS inasmuch as they are active against HIV.

The anti-HIV activity of the compounds of formula I and VI can be shown by the following test protocol:

TEST I-INHIBITION OF PROTEOLYTIC ACTIVITY OF HIV-1-PROTEASE

The ability of compounds of the invention to inhibit the proteolytic activity of HIV-1 protease was determined by using the method of Louis, et al., Biochem. Biophys. Res. Comm. 159:87–94, (1989), which is herein incorporated by reference. In using the method of Louis et al., HIV Substrate III, His-Lys-Ala-Arg-Val-Leu-pNO $_2$Phe-Glu-Ala-Nle-Ser-$NH_2$ purchased from Bachem Bioscience, Inc. Philadelphia, Pa. was used in place of the nonapeptide substrate Val-Ser-Gln-Asn-Tyr-Pro-Ile-Val-Gln-amide.

TEST 2-INHIBITION OF THE GROWTH OF HIV-1 IN TISSUE CULTURE CELLS

This test measured the capability of the compounds to inhibit the growth of HIV-1 in tissue culture cells. CEM-SS cells (human T-lymphocyte derived tissue culture cells) were infected with HIV-1, isolate III B which was produced in tissue culture. After 7 days, the virus has killed the cells as monitored by extensive syncytia formation (cell fusion). The test measured the capability of the chemical synthetic compounds to prevent syncytia formation and cell death. CEM cells were grown at 37° C. in an atmosphere of 5% $CO_2$. HIV isolate III B was prepared by growth in and crude purification from CEM cells. The chemical synthetic compound was added to 96 well microtiter plates and diluted in varying steps across the wells of the plate. Cells and virus were added to each well and the concentration of the chemical synthetic compound required to inhibit syncytia formation by 50% (the $IC_{50}$) after 7 days was determined. The viability of CEM cells which are not infected with HIV-1 isolate III B was simultaneously determined by the MTT assay, as described in Mossman, J. Immunolog. Methods 65:55–63, 1983, which is herein incorporated by reference.

$IC_{50}$'s in Test 1 (Protease Activity) and Test 2 (Anti-HIV) above, for a sedes of compounds of formulas I of the invention are shown in Table 1 below. Mass spectrum (MS) numbers are also shown Table 1. Compound numbers correspond to the numbers that were assigned above.

TEST 3-INHIBITION OF PROTEOLYTIC ACTIVITY OF HIV-1-PROTEASE AS DETERMINED BY SCINTILLATION PROXIMITY ASSAY (SPA).

This is an alternative assay to test #1 and is used to determine the ability of compounds to inhibit the HIV1 protease activity. The SPA assay for HIV1 protease has been developed by Amersham Corporation, Arlington Heights, Ill., and is available for commercial use. In this system the substrate for HIV1 protease, AcN-(I $^{125}$)Tyr-Arg-Ala-Arg-Val-Phe-Phe-Val-Arg-Ala-Ala-Lys-SPA bead, is cleaved by the HIV1 protease at the Phe-Phe bond releasing the $I^{125}$-labelled peptide fragment from the SPA bead. This event causes removal of detectable signal from the microsphere bead indicated by reduction in radioactivity (measured in CPM), which is proportional to the proteolytic activity. The substrate, and the HIV 1 protease were incubated in presence of synthetic compound in various dilutions at room temperature for 40 minutes, and the concentration of the compound required to inhibit the proteolytic activity by 50% ($IC_{50}$) was determined.

| | Enzyme Assays | | | |
|---|---|---|---|---|
| Compound | (HPLC) IC$_{50}$ µg/ML or nM as shown below | (SPA) IC$_{50}$ µg/ML or nM as shown below | HIVMIC IC50 µg/ML | Physical Data |
| 1 | >50 nM | — | — | FABMS MH$^+$, 545.5 |
| 2 | <500 nM | — | 7.99 | FABMS M$^+$ +23 (Na), 664 |
| 3 | 54 nM | — | 0.537 | M$^+$ +23 (Na), 664.3 |
| 4 | 10 nM | — | 1.7 | MH$^+$, 626.5 |
| 5 | 8 nM | — | 1.77 | HRFABMS MH$^+$, 626.2984 C$_{35}$H$_{40}$N$_5$O$_6$ requires 626.2978 |
| 6 | — | >500 nM | — | HRFABMS MH$^+$, 627.2946 C$_{34}$H$_{39}$N$_6$O$_6$ requires 627.2931 |
| 7 | 50 nM | — | 5.69 | HRFABMS MH$^+$, 642.2859 C$_{35}$H$_{40}$N$_5$O$_7$ requires 642.2927 |
| 8 | 400 nM | — | 28.1 | FABMS MH$^+$, 642.4 |
| 9 | >500 nM | — | — | FABMS MH$^+$, 674.3 |
| 10 | — | 110 nM | — | HRFABMS MH+, 676.3152 C$_{39}$H$_{42}$N$_5$O$_6$ requires 676.3135 |
| 11 | — | 280 nM | — | HRFABMS MH$^+$, 676.3171 C$_{39}$H$_{42}$N$_5$O$_6$ requires 676.3135 |
| 12 | — | 230 nM | — | HRFABMS MH$^+$, 676.3164 C$_{39}$H$_{42}$N$_5$O$_6$ requires 676.3135 |
| 13 | 300 nM | — | 5.07 | FABMS MH$^+$, 634 |
| 14 | — | >200 nM | — | FABMS MH$^+$, 654.5 |
| 15 | — | >200 nM | — | mp 180-2° C. |
| 16 | >500 nM | — | — | FABMS MH$^+$, 654.6 |
| 17 | — | 200 nM | — | FABMS MH$^+$, 654.2767 C$_{36}$H$_{40}$N$_5$O$_5$S requires 654.2750 |
| 18 | >500 nM | — | — | FABMS MH$^+$, 654. |
| 19 | — | 196 nM | — | HRFABMS MH$^+$, 654.2773 C$_{365}$H$_{40}$N$_5$O$_5$S requires 654.2750 |
| 20 | 74 nM | — | 6.26 | FABMS Mh$^+$ +23 (Na) = 676 |
| 21 | — | >200 nM | — | HRFABMS MH$^+$, 654.2767 C$_{36}$H$_{40}$N$_5$O$_5$S requires 654.2750 |
| 22 | — | >200 nM | — | FABMS MH$^+$, 583.6 |
| 23 | — | >200 nM | — | HRFABMS MH$^+$, 642.4 |
| 24 | — | >200 nM | — | HRFABMS MH$^+$, |

| Compound | (HPLC) IC$_{50}$ µg/ML or nM as shown below | (SPA) IC$_{50}$ µg/ML or nM as shown below | HIVMIC IC50 µg/ML | Physical Data |
|---|---|---|---|---|
| | | | | 642.2767 C$_{35}$H$_{40}$N$_5$O$_5$S requires 642.2750 |
| 25 | — | >200 nM | — | FABS MH$^+$, 642 |
| 26 | — | >200 nM | — | HRFABMS MH$^+$, 642.2761 C$_{35}$H$_{40}$N$_5$O$_5$S requires 642.2750 |
| 27 | >500 nM | — | — | FABMS MH$^+$, 594.4 |
| 28 | — | >200 nM | — | See NMR data |
| 29 | — | >200 nM | — | FABMS MH$^+$ +23 (Na) = 742 |
| 30 | >50 nM | | | FABMS MH$^+$, 720 |
| 32 | >50 nM | — | — | FABMS MH$^+$, 625.4 and M$^+$ +23 (Na) 647.4 |
| 33 | >500 nM | — | NA | FABMS MH$^+$, 675.5 |
| 34 | — | >200 nM | — | HRFABMS MH$^+$, 675.3016 C$_{40}$H$_{43}$N$_4$O$_4$S requires 675.3005 |
| 35 | 26 nM | — | 2.1/NA* | MH$^+$ 641.5 |
| 36 | — | 132 nM | — | HRFABMS MH$^+$, 641.3173 C$_{37}$H$_{45}$N$_4$O$_4$S requires 641.3162 |
| 37 | 60 nM | — | 6.08 | HRFABMS MH$^+$, 625.3404 C$_{37}$H$_{45}$N$_4$O$_5$ requires 625.3990 |
| 38 | — | >500 nM (46% inhibition) | — | HRFABMS MH$^+$, 625.3402 C$_{37}$H$_{45}$N$_4$O$_5$ requires MH+ 625.3390 |
| 39 | — | >200 nM | — | HRFABMS MH$^+$, 641.3172 C$_{37}$H$_{45}$N$_4$O$_4$S requires MH+ 641.3161 |
| 41 | >100 nM | — | — | FABMS MH$^+$, 670.3 |
| 42 | — | >200 nM | — | HRFABMS MH$^+$, 670.3051 C$_{37}$H$_{44}$N$_5$O$_5$S requires 670.3063 |
| 43 | >100 nM | — | — | HRFABMS MH$^+$, 705.3133 C$_{41}$H$_{45}$N$_4$O$_5$S requires 705.3111 |
| 44 | >100 nM | — | — | HRFABMS MH$^+$, 659.2708 C$_{36}$H$_{43}$N$_4$O$_4$S$_2$ requires 659.2726 |
| 45 | >100 nM | — | — | FABMS MH$^+$, 722.8 |
| 47 | >100 nM | — | — | HRFABMS MH$^+$, 642.2713 C$_{35}$H$_{40}$N$_5$O$_5$S requires |

-continued

| | Enzyme Assays | | | |
|---|---|---|---|---|
| | (HPLC) IC$_{50}$ µg/ML or nM as shown | (SPA) IC$_{50}$ µg/ML or nM as shown | HIVMIC | |
| Compound | below | below | IC50 µg/ML | Physical Data |
| 48 | >100 nM | — | — | 642.2750 HRFABMS MH$^+$, 656.2918 C$_{36}$H$_{42}$N$_5$O$_5$S requires 656.2907 |
| 49 | 80 nM | — | 19.4 | HRFABMS MH$^+$, 627.3021 C$_{36}$H$_{43}$N$_4$O$_4$S requires 627.3005 |
| 50 | >100 nM | — | NA | HRFABMS MH$^+$, 655.3337 C$_{38}$H$_{47}$N$_4$O$_4$S requires 655.3318 |
| 51 | >5 nM | — | NA | FABMS MH$^+$, 714.6 |
| 52 | — | 390 nM | 8.58 | FABMS MH$^+$, 641 |
| 53 | >100 nM | — | — | FABMS MH$^+$, 701.4 |
| 54 | >100 nM | — | — | FABMS MH$^+$, 592 |
| 55 | >100 nM | — | — | |
| 56 | >100 nM | — | — | |
| 57 | >100 nM | — | — | |
| 58 | >100 nM | — | — | FABMS MH$^+$, 607 |
| 59 | 5 nM | — | 1.41 | HRFABMS MH$^+$, 627.2922 C$_{34}$H$_{39}$N$_6$O$_6$ requires 627.2931 |
| 60 | — | 48 nM | — | HRFABMS MH$^+$, 627.2946 C$_{34}$H$_{39}$N$_6$O$_6$ requires 627.2931 |
| 61 | — | 410 nM | — | FABMS MH$^+$, 642 |
| 63 | — | >500 nM (35% Inhibition) | — | FABMS MH$^+$, 643 |
| 64 | — | >500 nM (36% Inhibition) | — | FABMS MH$^+$, |
| 65 | — | 500 nM | — | FABMS MH$^+$, 627 |
| 66 | — | 124 nM | — | FABMS MH$^+$, 627 |
| 68 | — | >500 nM (36% Inhibition) | — | FABMS MH$^+$, 658.6 |
| 69 | — | 84 nM | — | FABMS MH$^+$, 705 |
| 70 | — | 55 nM | — | FABMS MH$^+$, 705 |
| 71 | — | 245 nM | — | FABMS MH$^+$, 703 |
| 73 | — | 425 nM | — | FABMS MH$^+$, 661.5 |
| 75 | >500 nM | — | — | FABMS MH$^+$, 612 |
| 76 | — | >500 nM | — | FABMS MH$^+$, 640 |
| 77 | — | — | 17.5 | HRFABMS MH$^+$, 578.2989 |
| 78 | — | 230 nM | 0.68 | HRFABMS MH$^+$, 648.3233 |
| 79 | — | >500 nM | 9.1 | FABMS MH$^+$, 658.5 |

-continued

| | Enzyme Assays | | | |
|---|---|---|---|---|
| Compound | (HPLC) IC$_{50}$ µg/ML or nM as shown below | (SPA) IC$_{50}$ µg/ML or nM as shown below | HIVMIC IC50 µg/ML | Physical Data |
| IN 1 | — | 80 nM | 4.95 | HRFABMS MH$^+$, 605.3005 C$_{33}$H$_{41}$N$_4$O$_7$ requires 605.2975 |
| IN 2 | >100 nM | — | — | HRFABMS MH$^+$, 650.3276 C$_{36}$H$_{48}$N$_3$O$_6$S requires 650.3264 |
| IN 3 | >100 nM | — | — | FABMS MH$^+$, 601.2 |
| IN 4 | >100 nM | — | — | FABMS MH$^+$, 572 |
| IN 5 | >100 nM | — | — | HRFABMS MH$^+$ 604.2885 C$_{31}$H$_{46}$N$_3$O$_5$S$_2$ requires 604.2879 |
| IN 6 | >100 nM | — | — | FABMS MH$^+$, 659.5 |
| IN 7 | — | >500 nM | — | See Nmr Data |
| IN 8 | — | 125 nM | — | FABMS MH$^+$, 605.5 |

As used herein "——" means not tested. NA means not active. Certain compounds have been given the NA rating; however, it is believed that such compounds would be active when assayed under other conditions. One entry above is "2.1/NA". This means that one experiment resulted in an IC$_{50}$ of 2.1 µg/mL and another experiment resulted in a finding of no activity.

As used herein, FABMS means fast atom bombardment mass spectrogram. HRFABMS means high resolution fast atom bombardment mass spectrogram. As indicated in the table above, certain of the mass spectrograms are done with hydrogen, and others are done with sodium.

NMR data for compound 28, is as follows:

δH(400 MHz; d$_6$-DMSO) 1.25 (9H, s, C(CH$_3$), 2.30 (2H, t, J=7.5), 2.43–2.76 (7H, m,), 2.96 (1H, dd, J=13.8 and 3.0), 3.50–3.60 (1H, m), 3.87–3.97 (1H, m), 4.66–4.75 (1H, m) 5.09 (1H, d, J=6.4) 6.92–6.98 (2H, m) 7.02–7.08 (2H, m) 7.14–7.19 (2H, m) 7.42–7.48 (2H, m ), 7.72–7.77 (1H, m) 7.87–7.96 (2H,m), 8.12 (2H, t, J=8.9), 8.19 (1H, d J=8.5), 8.60 (1H, d, J=8.5) and 8.85(1H, d, J=8.1).

NMR data for intermediate 7 is as follows:

δH(400 MHz; CDCl$_3$) 0.61 (3H, d, J=6.7, CHCH$_3$), 0.75 (3H, t, J=7.4, CH$_2$CH$_3$), 0.81–0.94 (1H, m), 1.12–1.24 (1H, m), 1.42 (9H, 1×C(CH$_3$)$_3$) 1.48 (9H, 1×C(CH$_3$)$_3$) 1.55–1.65 (1H, m) 2.72–2.89 (2H, m), 2.98–3.12 (2H, m) 3.53∝3.59 (1H, m), 3.71 (1H, dd, J=8.8 and 6.2), 4.23–4.32 (1H, m) 4.99 (1 H, br.d) 5.87 (1 H, br.s) 5.94 (1 H, br.d.) 7.13–7.40 (9H, m), and 7.54 (1H, d, J=7.7).

The IC$_{50}$s in the Table above indicate that the compounds of formula I are active against HIV and are therefore useful in treating AIDS.

The intermediate compound

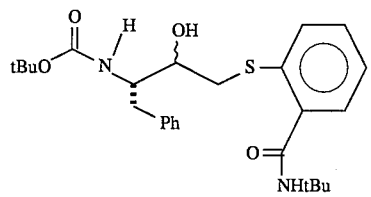

is also active against HIV-1 having an IC$_{50}$ of 3 µM in Test 1-Inhibition of Proteolytic Activity of HIV-1-Protease.

The compounds of this invention can be administered in any number of conventional dosage forms, e.g., oral, parenteral, rectal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, solubilizing agents, emulsifying agents, dispersing agents, suspending agents, perfumes, preservatives, lubricants, etc.

Suitable pharmaceutical acceptable solid carriers are magnesium carbonate, magnesium stearate, talc, sugar, lactose, pectin, dextrin, cyclodextrins α, β, and γ and their derivatives, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may be administered by any conventional mode of administration by employing an antiviral effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antiviral activity. For example, when administered orally doses of from about 20 to about 60 mg/kg of body weight may be used; and when administered parenterally, e.g., intravenously, dosages of from about 5 to about 20 mg/kg body weight may be used.

The dosage to be administered and the route of administration depends upon the particular compound used, the age and general health of the patient and the severity of the viral condition. Thus, the dose ultimately decided upon must be left to the judgment of a trained health-care practitioner.

The compounds of this invention may also be administered concurrently with other known anti-viral agents such as AZT. The compounds of this invention may also be administered either before or after the administration of other known antiviral agents such as AZT. The just above mentioned combination therapies is believed to result in a synergistic action between the particular compound of the invention, and the other anti-HIV agent administered.

The invention disclosed herein is exemplified by the following preparative examples, which should not be construed to limit the scope of the disclosure. Alternative mechanistic pathways and analogous structures within the scope of the invention may be apparent to those skilled in the art.

EXAMPLE 1

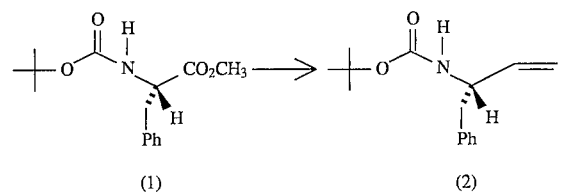

Methyl ester (1), which is known or can be prepared in accordance with known methods, was reduced using DIBAL-H according to the procedure of Rich et al., J. Org., Chem., 43, 3624 which is hereby incorporated by reference.

98.5 ml of a 1.0M solution of diisobutylaluminum hydride (DIBAL -H)was added to a stirred solution of methyl ester (1) (11.00 g) in 170 ml of toluene at −78° C. (dry ice/acetone bath), under an atmosphere of nitrogen. The resulting mixture was stirred at that temperature for 6 minutes and then 10 ml of methanol was added followed by treatment with Rochelle salt.

The resulting crude aldehyde (containing about 10% of the overreduced alcohol) was not purified but used directly in the next step of the synthesis.

78.8 ml of a 1.0M solution of sodium hexamethyldisilazide (NaHMDS) in tetrahydrofuran (THF) was added dropwise to a stirred suspension of 28.17 g of methyltriphenylphosphonium bromide in THF (320 ml) at room temperature under an atmosphere of nitrogen. After stirring for one half hour, the crude aldehyde in THF (about 5 ml) was added and stirred for another 3 hours. The reaction was partitioned between ethyl acetate and water. The organic phase was separated, dried, and concentrated to give 25.27 g of a crude product which was dissolved in chloroform and preadsorbed on silica gel (about 50 g) before purification by column chromatography, using ethyl acetate-hexane(1:10) as the eluant. This reaction gave the alkene (2)(6.7 g) as a white solid.

EXAMPLE 2

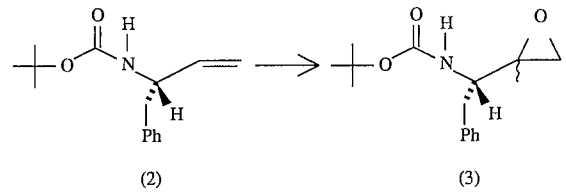

9.12 g of 80% meta-chloroperoxybenzoic acid (MCPBA) was added slowly to a stirred solution of 6.47 g of alkene (2) in 250 ml of chloroform at 0° C. (ice bath temperature), under a nitrogen atmosphere. When the addition was complete, the mixture was allowed to warm to room temperature overnight.

The reaction mixture was partitioned between ethyl acetate and 10% sodium sulfite. The organic phase was separated, washed with sodium sulfite and saturated aqueous NaHCO₃, dried and concentrated to give 6.49 g of the title compound.

EXAMPLE 3

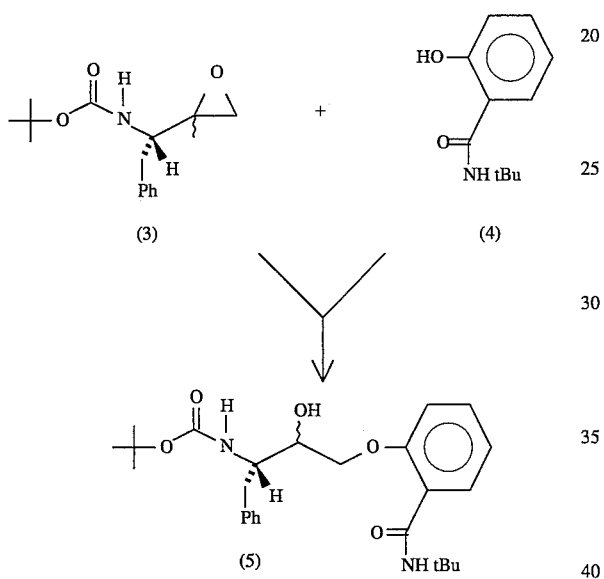

27.2 mg of phenol (4) and 37.0 mg of epoxide (3)in dimethylformamide (DMF) (1 ml) were heated to 120° (oil bath) under an atmosphere of nitrogen overnight (about 20 hours). After cooling the brown solution was partitioned between ethyl acetate and water. The organic layer was separated, washed with water (X3), dried and concentrated.

Plate chromatography (plc) of the residue using ethyl acetate-hexane (4:6) as eluant gave the ether (5) (14.4 mgs). Still a considerable amount of starting material was left but not isolated.

EXAMPLE 4

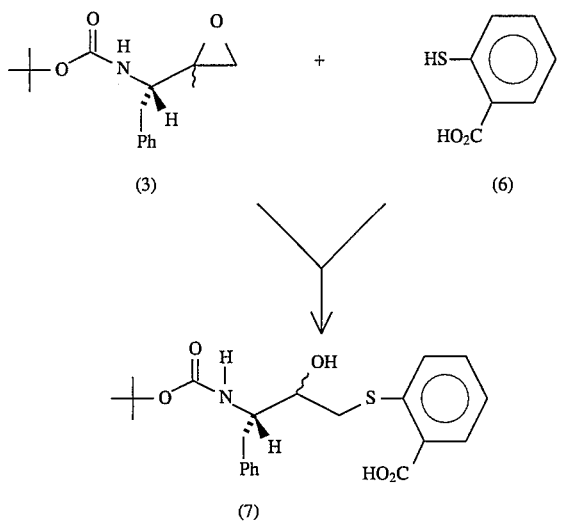

0.37 g of sodium hydroxide was added to a stirred solution of 1.109 g of the epoxide (3) and 0.65 g of thiosalicylic acid (6) in ethanol, at room temperature, under an atmosphere of nitrogen. The resulting mixture was stirred at room temperature until thin layer chromatography (tlc) indicated that no epoxide (3) remained (about 2.5 hours). The mixture was partitioned between ethyl acetate and 5% HCl. The organic phase was separated, washed with water and worked up. The work-up gave 1.6619 g (95%) of a white foam (7) which was used in next step without purification.

EXAMPLE 5

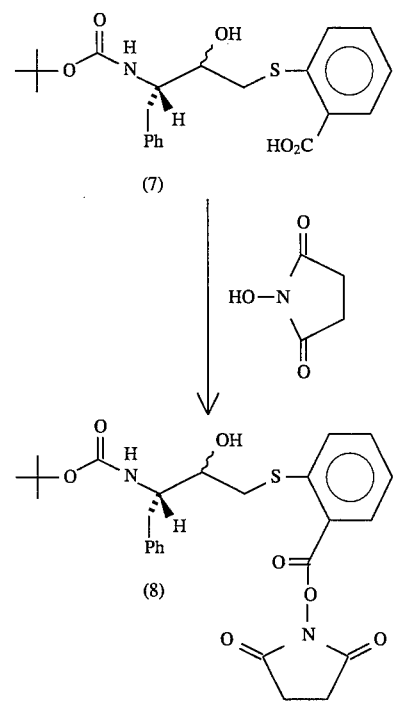

0.871 g of 1,3-dicyclohexylcarbodiimide (DCC) was added to a stirred solution of 1.6009 g of acid (7) and 0.486 g of N-hydroxy succinimide in tetrahydrofuran (THF) (30 ml) at room temperature, under an atmosphere of nitrogen. The resulting mixture was stirred for 16 hours, and partitioned between ethyl acetate and water. The organic phase was separated, washed with water (X2) and worked up.

The work-up gave 2.219 g of (8) (112%; contains some DCU) as a white foam. The material was used in next step without purification.

EXAMPLE 6

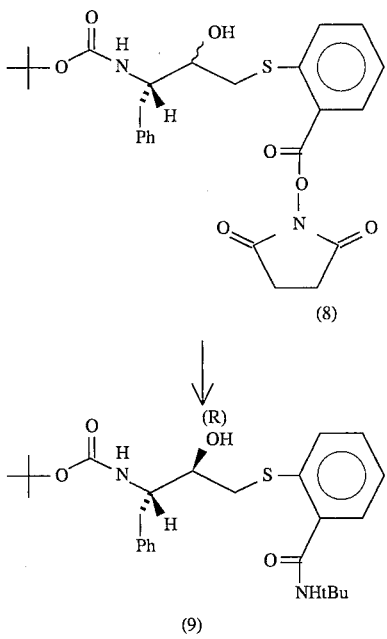

0.43 ml of t-BuNH₂ was added dropwise to a stirred solution of 0.7033 g of succinimidyl ester (8) in 15 ml of dioxane at room temperature, under an atmosphere of nitrogen. The resulting mixture was stirred for 5.5 hours, partitioned between ethyl acetate and water. The organic phase was separated, washed with water (X2), dried and worked up.

Column chromatography of the crude reaction product using EtOAc-hexane (3:7) as eluant gave the desired product (9) (0.3170 g)

EXAMPLE 7

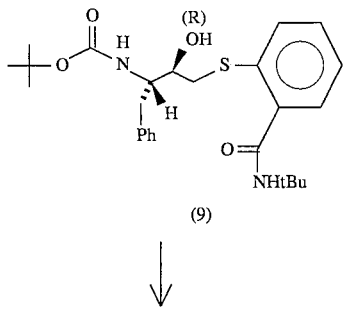

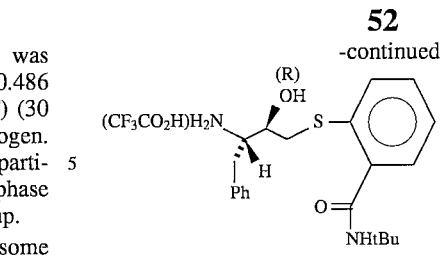

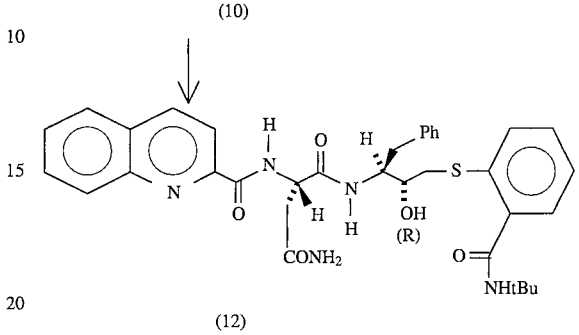

1. First step - acidolysis

½ ml. of trifluoroacetic acid (TFA) was added to a $CH_2Cl_2$ solution of 18.9 mg of the carbamate (9), at 0° C. (ice bath), under an atmosphere of nitrogen. The resulting solution was maintained at 0° for ½ hr. and then the volatiles were removed under reduced pressure to give the salt (10) 19.5 mg. (100%).

2. Second step coupling 0.020 g of benzotriazol-1-yloxytris(dimethylamino)phosphonium hexafluorophosphate (BOP reagent) followed by Et₃N (24 microliters) was added to a stirred solution of 0.0195 g of the salt (10), 0.0130 g of the acid (11)

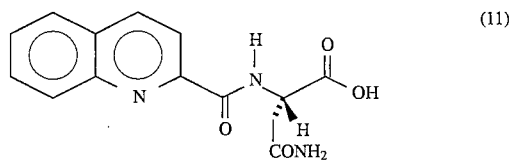

in ½ ml of $CH_2Cl_2$. The resulting mixture was stirred at room temperature, under an atmosphere of nitrogen for 16 hours. The volatiles were removed under reduced pressure and the residue purified by plc using 2X EtOAc-MeOH (5:1) as eluant to give the desired product (12) (16.0 mgs; 62% overall) as an off-white solid.

The remaining —S— containing compounds specifically set forth in the tables above, were prepared by using methods analogous to those of examples 4, 5, 6, and 7.

EXAMPLE 8

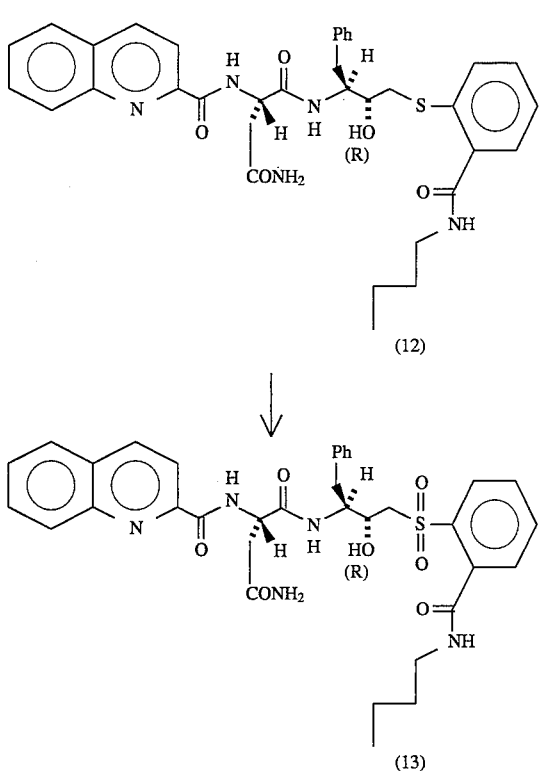

16.6 mg (2 equivalents) of about 80% MCPBA was added in one portion to a stirred solution of the 16.4 mg of sulfide (12) (1 equivalent) in 1 ml chloroform at room temperature. The resulting mixture was stirred for 72 hours, concentrated, and the residue purified by plc, using (2x EtOAc:MeOH 10:1) as the eluant.

The title compound (13) was obtained as a white solid. (10.1 mg; 59%).

Sulfide (12) was obtained by procedures analogous to those set forth in examples 4, 5, 6, and 7.

Compounds wherein Y is —SO— may be obtained by methods analogous to those set forth in Example 8 above, except that 1 equivalent of sulfide are employed as against one equivalent of MCPBA. Both R- and S-sulfoxides are formed in this reaction.

EXAMPLE 9

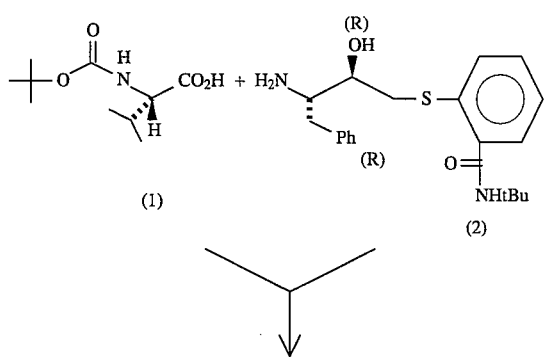

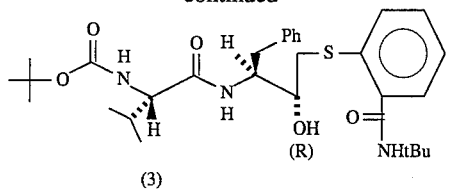

Starting with 97.5 mg of acid (1), and 0.16 g of the hydroxyamine (2) and following the procedure in Example 27 below, the peptide (3) (0.2338 g; 94%) was obtained as a white solid after column chromatography. EtOAc/hexane (4:6) was used as the eluant.

EXAMPLE 10

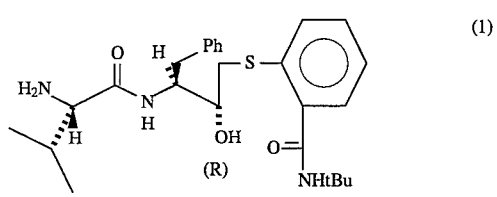

Starting with 0.1513 g of the carbamate from the previous example, and following the procedure set forth in Example 26 below, the amine (1) (92.2 mg; 74%) was obtained. This product was used in the next step without purification.

EXAMPLE 11

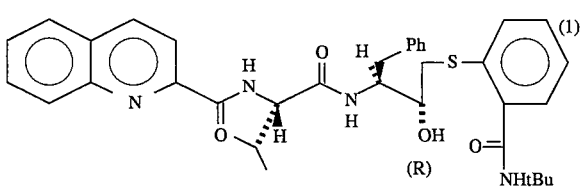

Starting with 0.0753 g of the hydroxyamine from the previous example, 0.0277 g of quinaldic acid and following the procedure set forth in Example 27 below, the peptide (1) (0.0905 g; 91%) was obtained as a white semi-solid after column chromatography. EtOAc/hexane (1:1) was used as the eluant.

EXAMPLE 12

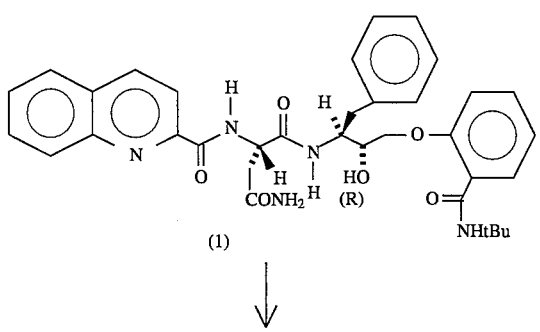

-continued

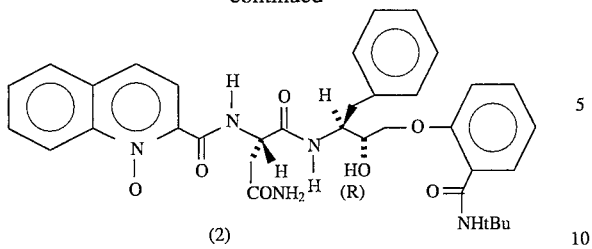

(2)

16.6 mgs of about 80% pure meta-chloroperbenzoic acid (MCPBA) was added to a stirred solution of 30.0 mgs of the amine (1) in 1 ml of chloroform and the resulting solution was stirred at room temperature for 1 week. The reaction was partitioned between EtOAc and 10% aqueous sodium thiosulfate. The organic phase was separated, washed with aqueous sodium thiosulfate (X3) then saturated aqueous sodium bicarbonate. The organic phase was dried and concentrated. Column chomatography of the crude reaction product using EtOAc-MeOH (20:1) gave the N-oxide (2) (19.7 mgs; 64%) as a white powder.

EXAMPLE 13

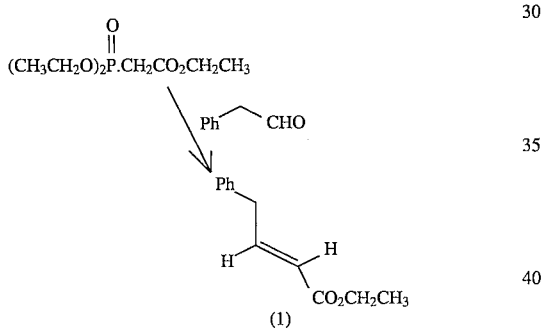

5.14 g KOtBu was added to a stirred solution of 11.21 g triethylphosphonoacetate in 100 ml tetrahydrofuran (THF). The mixture was cooled in an ice bath, under an atmosphere of nitrogen. When the addition was complete the resulting mixture was stirred at room temperature for 1 hour, cooled to −78° stirred for a further ½ hour and then 5.00 g phenyl acetaldehyde was added. The mixture was stirred at −78° for ½ hour, poured into EtOAc and saturated ammonium chloride followed by aqueous work-up. EtOAc hexane (1:10) column chromatography of the crude reaction product gave the (E) - alkene (1) (4.33 g; 55%) as a colorless oil, essentially a single diastereomer, ethyl (E) - 4- Phenyl- but-2- enoate.Vmax|CM$^{-1}$ (CHCl$_3$), 1705, 1655 and 1603. δH (400 MHz; CDCl$_3$), 1.27 (3H, t, J=7.1, CO$_2$CH$_2$CH$_3$), 3.52 (2H, dd, J=6.9 and ca. 1.3, CH$_2$ Ph), 4.18 (2H, q, J=7.1, CO$_2$CH$_2$CH$_3$), 5.81, (1H, dt, J=15.6 and ca 1.7), 7.09 (1H, dt, J=15.6 and 6.8) and 7.15–7.33 (5H, m, aryl C-H)

EXAMPLE 14

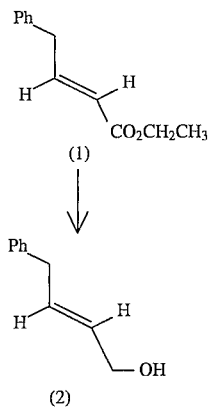

50 ml of a 1.0M solution (CH$_2$Cl$_2$) of DIBAL-H was added to a stirred solution of 4.28 g of ester (1) at −78° in CH$_2$Cl$_2$ (100 ml ) under an atmosphere of nitrogen. The resulting mixture was stirred for ½ hour and warmed to room temperature. After aqueous workup the crude reaction product was purified by column chromatography using (EtOAc-hexane; 1:5) as eluant to give the desired allylic alcohol (2) (3.12 g, 95%) as a colorless oil.

(E) -4- Phenylbut-2-en-1-ol Vmax|cm$^{-1}$ (CHCl$_3$) 3060, δH (400MH$_z$ CDCl$_3$), 1.90 (1H, brs, OH), 3.38 (2H, d, J=6.7, CH$_2$Ph), (4.10) 2H, appdq, J=5.8 and ca. 1.2, CH$_2$OH), 5.64–5.74 (1H, m) 5.80–5.89 (1H, m). and 7.13–7.40 (5H, m, aryl C-H).

EXAMPLE 15

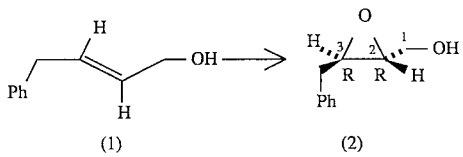

Starting with allylic alcohol (1) (2.90 g), and (D)-(−)-diethyl tartrate a procedure analogous to the procedure in Katsuki and Sharpless J. Am. Chem. Soc., 1980, 102,5974 and N. L. Lentz and N. P. Peet in Tetrahedron Letters, 1990, 31, 811 was followed to give crude reaction product (2). These publications are herein incorporated by reference. Column chromatography (EtOAc:hexane (3:7)) of the crude reaction product gave the desired epoxide (2) (2.69 g, 84%) as a colorless oil.

(2R, 3R) -3-Benzyloxirane methanol- Vmax|cm$^{-1}$ (CHCl$_3$) 3060, δH (400MH$_z$;CDCl$_3$), 2.27 (1H, brs, OH), 2.84 (1H, dd, J=14.5 and 5.3, 1×CH$_2$Ph),2.93(1H, dd, J=5.8and 14.5, 1×CH$_2$Ph),2.96–2.99 (1H, m. 1×CHO), 3.16–3.20 (1H, m, 1×CHO), 3.58 (1H, dd, J=12.8 and 4.3, 1×CH$_2$OH), 3.87 (1H, dd, J=12.8 and 2.2. 1×CH$_2$ OH) and 7.20–7.33 (5H, m, aryl C-H)

EXAMPLE 16

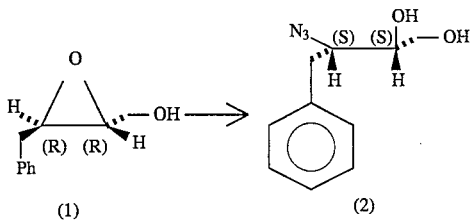

Starting with 2.26 g of epoxide (1) and following the procedure and workup as described in *Shamless et. al., J. Org. Chem.,* 1988, 53, 5187 gave the azide-diol 2.03 g (71%) after column chromatography. This publication is herein incorporated by reference.

δH (400MHz; CDCl$_3$), 2.33 (2H, br.s, 2XOH), 2.80 (1H, dd, J=9.1 and 14.1), 3.06 (1H, dd J=4.1 and 14.1) 3.64–3.83 (4H, m) and 7.20–7.47 (5H, m)

EXAMPLE 17

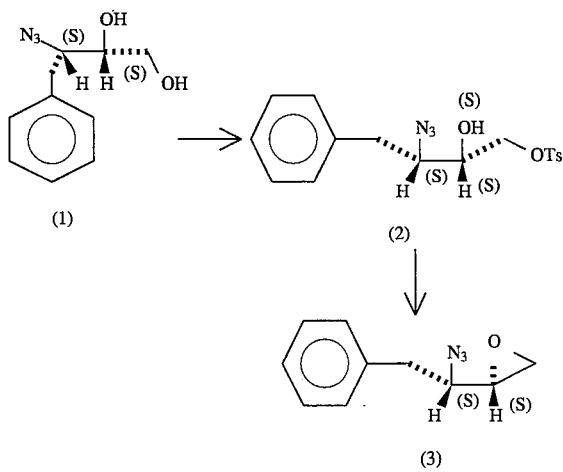

0.524 g of tosylchloride was added slowly to a stirred solution of 0.5631 g diol (1) in 5 ml pyridine at 0° C. (ice bath) and when the addition was complete the resulting mixture was stirred at room temperature for 3 hours, and poured into EtOAc - 5% aq HCl. The organic phase was separated, washed with 5% aq HCl, saturated aqueous NaHCO$_3$, dried and concentrated. Column chromatography of the crude reaction product using EtOAc- hexane (1:10) as eluant gave the intermediate tosylate (0.527 g, 53%).

The tosylate (2) (0.527 g; 1.5 mmol)in DMF ($_2$ ml) was added to a stirred solution of sodium hydride (84 mgs of a 50% dispersion in mineral oil (18 mmol; washed twice with hexanes) in DMF (5 ml) cooled in an ice bath, under an atmosphere of nitrogen. The resulting mixture was stirred for ½ hour, and partitioned between EtOAc and water. The organic phase was separated, dried and concentrated. Column chromatography of the crude reaction product using EtOAc-hexane (1:20) gave the desired epoxide (3) (0.1843 g; 67%) as a colorless oil. As used herein Ts means tosylate.

δH (400MH$_z$; CDCl$_3$), 2.79–2.85 (3H, m) 2.99 (1H, dd, J=4.6 and 14.0), 3.04–3.08 (1H, m), 3.57–3.62 (1H, m) and 7.20–7.37 (5H, m)., [α]D$^{20}$=+14.3° (C,1.3; CHCl$_3$) in excellent agreement with the same compound prepared by A. K. Ghosh et. al. J. Chem. Soc. Chem. Common., 1992, 273. This publication is herein incorporated by reference.

EXAMPLE 18

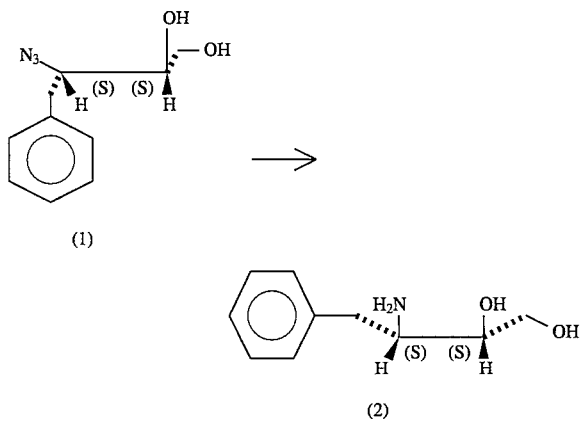

A suspension of 1.37 g of azide - diol (1) and 250 mg of the catalyst 10% Pd-C in 50 ml ethanol was placed under an atmosphere of hydrogen at room temperature for a pedod of 16 hours. The black suspension was filtered through a pad of celite and the solid was washed thoroughly with ethyl acetate. Concentration of the flitrate gave the crude amino - diol (2) (1.05 g; 87%) which was used in the next step without purification.

δH (400 MHz; CDCl$_3$), 2.61 (1H, dd, J=10.1 and 13.4), 2.74 (4H, brs), 2.93 (1H, dd J=4.2 and 13.4), 3.30–3.36 (1H, m), 3.60–3.65 (1H, m), 3.76 (1H, dd, J=3.9 and 11.8), 3.91 (1H, dd, J=4.4 and 11.8), and 7.15–7.36 (5H, m).

EXAMPLE 19

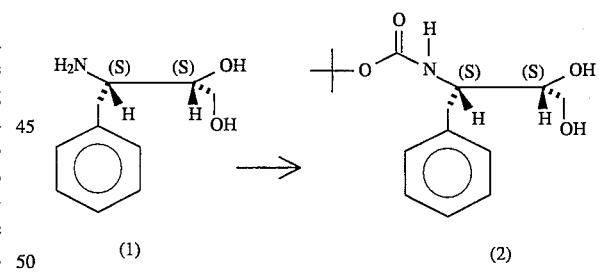

0.98 ml of Et$_3$N was added dropwise to a stirred solution of 1.046 g of amine (1) and 1.402 g of pyrocarbonate in 25 ml of dioxane. The mixture was cooled in an ice bath under an atmosphere of nitrogen. When the addition was complete the resulting mixture was stirred at room temperature for 3 hours. The reaction was concentrated and the residue was purified by column chromatography using EtOAC-hexane (6:4) as eluant to give the desired carbamate (2) (1.31 g; 80%) as a white foam. HRFABMS (MH+, 282.1707. C$_{15}$H$_{24}$NO$_4$ requires MH$^{+,}$ 282.1705).

EXAMPLE 20

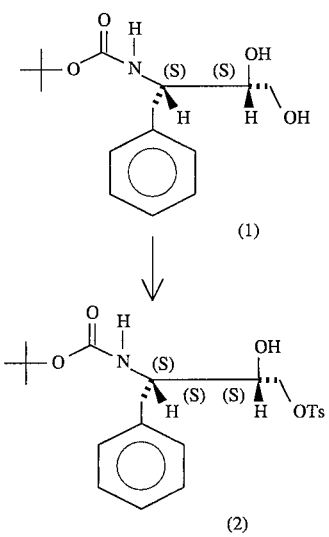

29 mgs of DMAP was added to a solution of 1.31 g of diol (1) and 0.895 g of tosylchloride in 15 ml of pyddine at 0° C. (ice bath) under an atmosphere of nitrogen. The resulting solution was stirred at room temperature for 3 hours, poured into 5% aqueous HCl solution and the organics extracted into EtOAc. The crude reaction product was purified by column chromatography (EtOAc-hexane 6:4) to give the tosylate 0.8354 g (41%) as a white solid.

Also 0.5315 g (41%) of starting material was recovered.

EXAMPLE 21

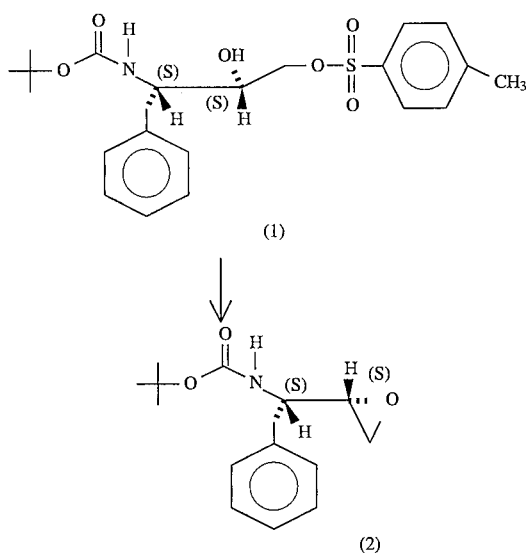

A solution of 0.8237 g tosylate (1) in 5 ml of dimethylformamide (DMF) (2 ml) was added to a stirred suspension of NaH, 183 mgs of a 50% dispersion of NaH in mineral oil, (and washed twice with hexane) in DMF, at 0° C. under an atmosphere of nitrogen. The resulting mixture was stirred at room temperature for ½ hour, partitioned between EtOAc and water followed by aqueous work-up.

Column chromatography of the crude product using EtOAc-hexane (1:5) as eluant gave the epoxide(2) (0.4217 g; 84%) as a white solid. mpt 123°–124° C. δH (400MHz; CDCl₃), 1.40 (9H, s, C(CH₃)₃, 2.73–2.94 (4H, m), 2.98 (1H, dd, J=5.2 and 14.0), 3.70 (1H, brs), 4.44 (1H, brs) and 7.20–7.37 (5H,m) in good agreement with the same compound prepared by a different route in the following reference. B. E. Evans J. Org. Chem., 1985, 50, 4615.

EXAMPLE 22

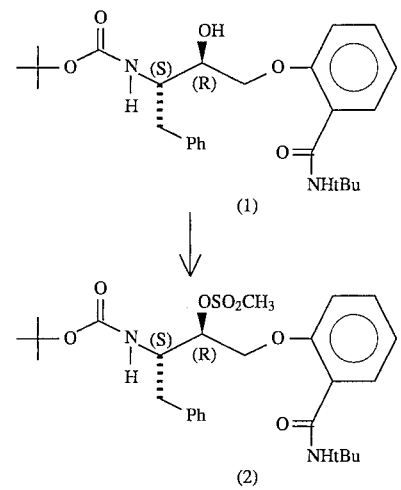

124 µl of Et₃N was added dropwise to a stirred solution of 0.2708 g of alcohol (1) and 51 µl of mesylchloride in 5 ml of dichloromethane at room temperature. The resulting mixture was stirred for 3 hours, partitioned between EtOAc and water. The organic phase was separated, washed with water (X2) dried and concentrated to give the mesylate (2) (0.306 g; 97%) as a white solid.

EXAMPLE 23

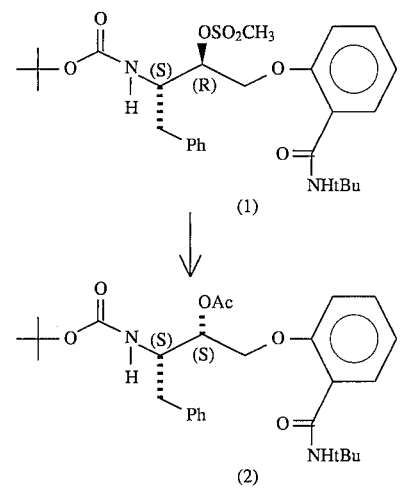

CsOAc was prepared as in, J. W. Huffman and R. C. Desai, Snyth. Commun., 1983, 13 (7), 553. using; Cs₂CO₃ 0.3204 g ). (0.98 mmol), AcOH (171 µl), MeOH 8 ml., mesylate (1) 0.3907 g (0.73 mmol), and DMF 4 ml. This publication was incorporated by reference. 0.3907g of mesylate (1) in 4 ml of dry DMF was added to the CsOAc and the resulting mixture was heated to 90° (oil bath) under an atmosphere of nitrogen, until tic indicated that no starting material (1) remained (about 3 hours.). After cooling, the mixture was partitioned between EtOAc and water followed by standard aqueous work-up.

Column chromatography of the residue gave the acetate (2) (0.2588 g; 71%) as a white solid. MH+, 499.2825. $C_{28}H_{39}N_2O_6$ requires MH+499.2808.

EXAMPLE 24

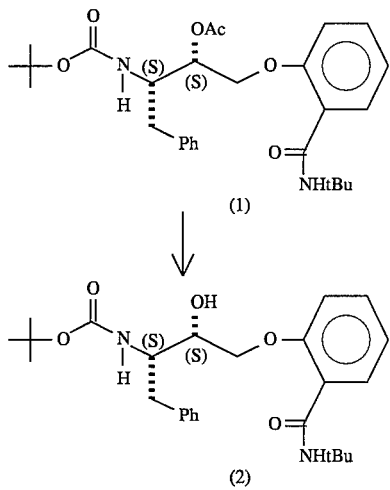

24 mgs of $K_2CO_3$ was added to a stirred solution of 0.2295 g of acetate (1) in 3 ml of MeOH at room temperature. The resulting mixture was stirred until thin layer chromatography (tlc) indicated that no starting material remained (after about 3 hours). The mixture was partitioned between EtOAc and water etc.

Column chromatography of the crude reaction product using EtOAc-hexane (3:7) as eluant gave the alcohol (2) (0.1664 g; 78%) as a white solid. FABMS MH+ 457.

EXAMPLE 25

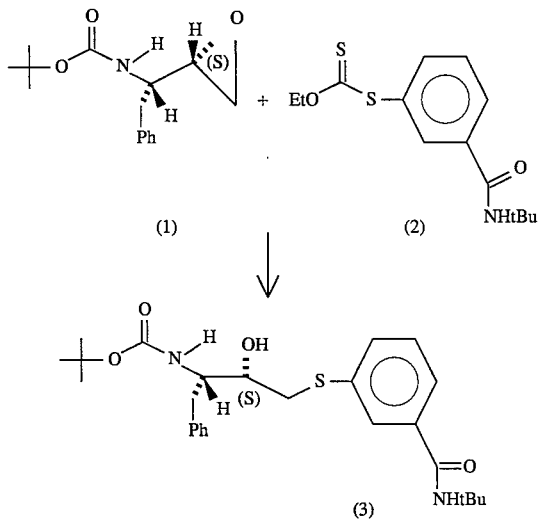

Sodium hydroxide (50.7 mg) was added to a solution of the epoxide (1) (0.101 g) and the xanthate (2) (0.114 g) in ethanol (5 ml) and water (1 ml). The resulting mixture was stirred at room temperature under an atmosphere of nitrogen for 3 hours and partitioned between EtOAc and water. Standard aqueous work-up and column chromatography on silica gel using EtOAc/hexane (3:7) as eluant gave the desired sulfide (3) (0.1446 g; 80%) as a white solid. HRFABMS. MH+, 473.2485. $C_{26}H_{37}N_2O_4S$ requires 473.2474.

EXAMPLE 26

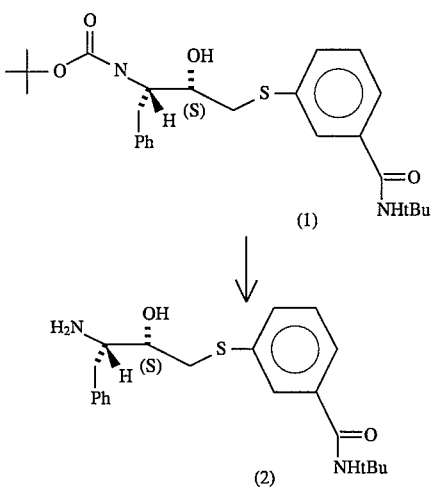

Trifluoroacetic acid (1 ml) was added to a stirred solution of the carbamate (2) (61.2 mg)in dichloromethane (1 ml) at room temperature under an atmosphere of nitrogen. The resulting mixture was stirred for 3 hours and the concentrated under reduced pressure. The residue was dissolved in EtOAc and excess $Et_3N$ was added. The organic phase was washed with water, dried and concentrated to give the crude hydroxy amine (2) (48 mg) as the final product. HRFABMS. MH+, 373.1953. $C_{21}H_{29}N_2O_2S$ requires 373.1950.

EXAMPLE 27

Triethylamine (2×0.11 mmol; added approximately one half hour apart) was added to a stirred suspension of the hydroxy amine (2) (41.4 mg), the acid (1)(35.1 mg) and BOP (54.1 mg) reagent in dichloromethane (1 ml). The resulting mixture was stirred at room temperature for 3 hours and partitioned between EtOAc and water. Standard aqueous work-up and crystallization of the crude reaction product from EtOAc gave the peptide (3) (27.2 mg) as the final product. HRFABMS. MH$^+$, 642.2761. $C_{35}H_{40}N_5O_5S$ requires 642.2750.

EXAMPLE 28

* means the absolute stereochemistry at these centers is not known, but the relative stereochemistry is known.

Starting with 0.197 g of epoxide (1) and 0.243 g of trans-racemic thioester (2) and following the procedure set forth in Example 25, the carbamates (3) and (4) were obtained as an inseparable mixture. A white solid (0.335 g; 93%)

EXAMPLE 29

-continued
* means that the absolute stereochemistry at these centers is not known, but the relative stereochemistry is known Starting with the carbamates from the previous example and following the procedure set forth in Example 26, the amines (1) and (2) were obtained as an inseparable mixture and as a pale-yellow viscous oil. The products 1 and 2 were used in the next example without purification.

Starting with the acid (1) (26.1 mg), the amines from the previous example (31.8 mg) and following a procedure analogous to that of Example 27, a crude reaction product was obtained which was purified by column chromatography on silica gel using EtOAc/MeOH (20:1) as the eluant. This gave a (i) nonpolar isomer (isomer A; 15.6 mg) mp 180°–182° C., (ii) a mixture of the two components(17.0 mg) and a (iii), a polar isomer (isomer B; 14.3 mg) HRFABS MH$^+$·654.2767-$C_{36}H_{40}N_5O_5S$ requires 654.2750.

EXAMPLE 31

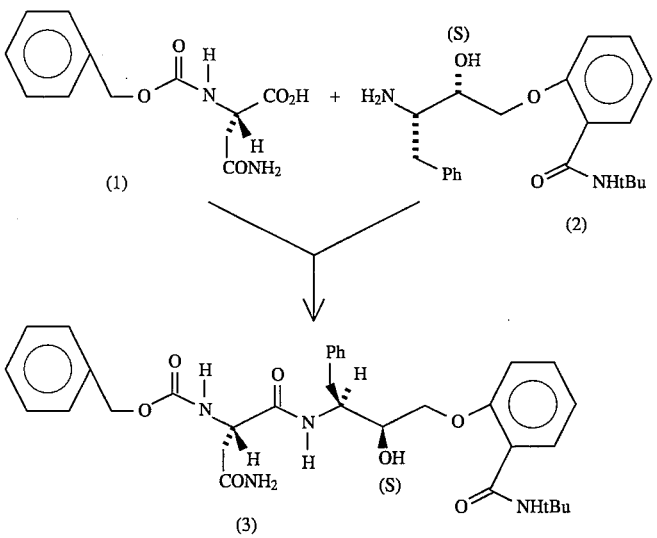

EXAMPLE 30

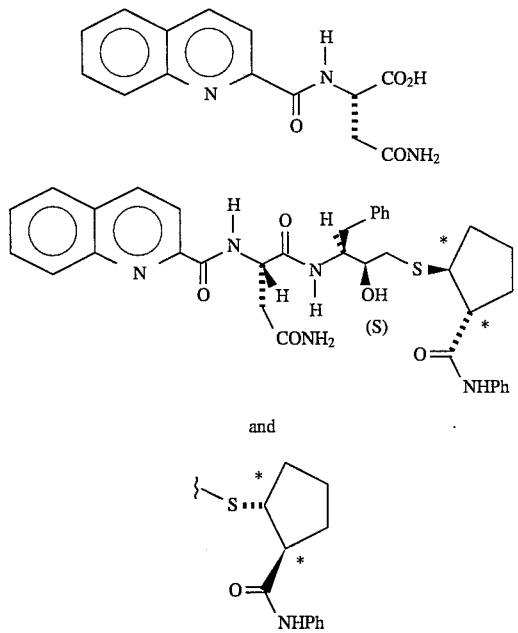

* means that the absolute stereochemistry at these centers is not known, but the relative stereochemistry is known Starting with the acid (1) (0.189 g), the hydroxyamine (2) (0.2413 g), and following the procedure set forth in Example 27, the adduct (3) (0.183 g; 46%) was obtained as a precipitate from the crude reaction product.

EXAMPLE 32

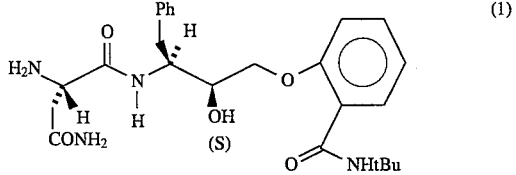

A suspension of the benzyl carbamate (from the previous example) (0.198 g) and 10% Pd-C (50 mg), in ethanol (10 ml) were placed under an atmosphere of hydrogen at room temperature overnight. The suspension was filtered through celite and the solid was washed thoroughly with Et OAc. Concentration of the filtrate gave the crude amine (1) (0.124 g) as a white solid. This product was used in the next step without purification. HRFABMS. MH$^+$, 471.2612. $C_{25}H_{35}N_4O_5$ requires 471.2607.

EXAMPLE 33

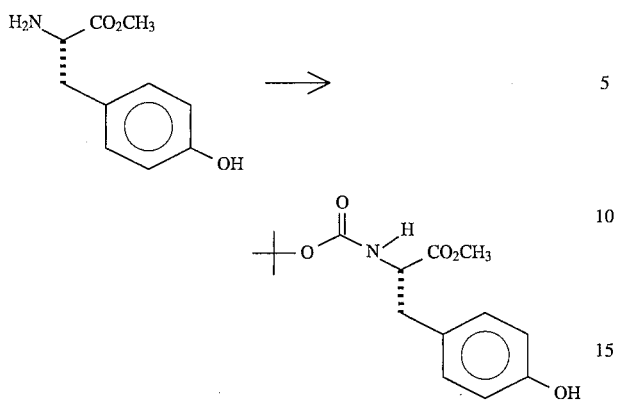

This procedure was carried out under nitrogen. To a solution of 10 g of amine (1) and 12.21 g of t-Butyl pyrocarbonate (2) in 250 ml of dioxane, was added 6.2 g (8.6 ml) of Et₃N dropwise with ice bath cooling. The reaction mixture was stirred for 3 hours, concentrated under reduced pressure, and the crude residue was chromatographed on SiO₂ column using (50% EtOAc/hexane) as eluent, 14.0 g of product was obtained.

EXAMPLE 34

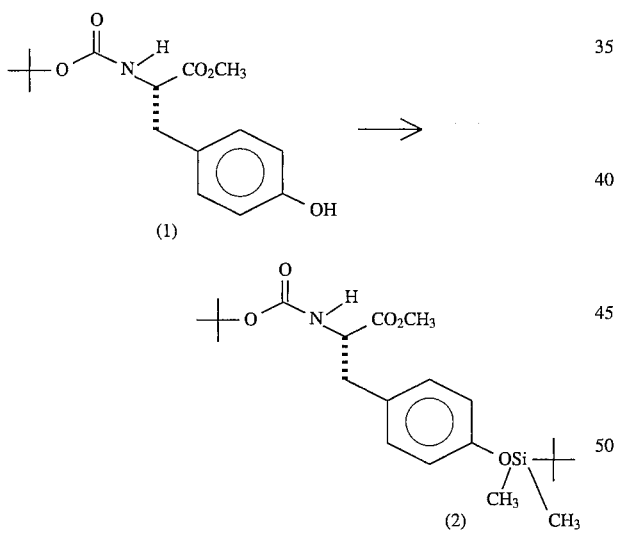

To a solution of 1.0 g. of hydroxy ester (1) in 10 ml. of DMF was added 0.56 g of t-butyl dimethyl silyl chloride (t-BDMS Cl), followed by 0.35 g. of imidazole, and the mixture was stirred at room temperature for two days.

The reaction mixture was partitioned between water (100 ml) and EtOAc (100 ml). The organic phase was washed with brine, dried (Na₂SO₄), and concentrated.

The residue was purified by SiO₂ column chromatography. 25% EtOAc/hexane. 1.3 g. of product (2) was obtained.

EXAMPLE 35

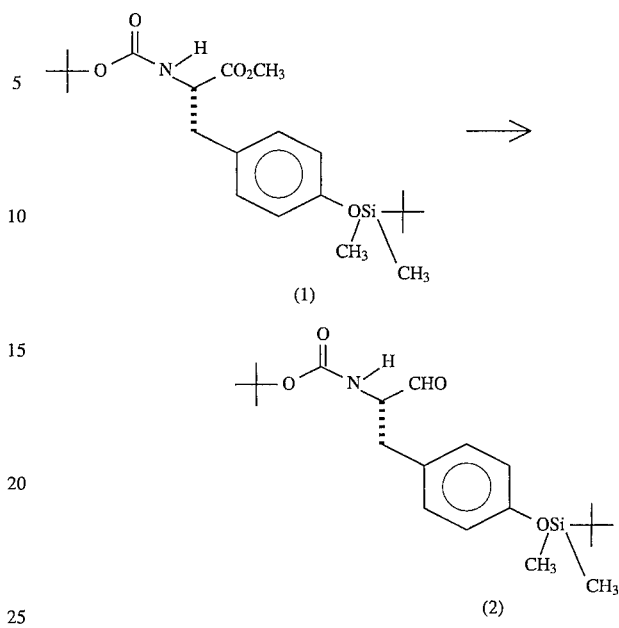

Procedure:

To a stirred solution of 0.6 g of ester (1) in 7 ml of toluene, at −78° C., was added 3.74 ml of a 1.0M solution of diisobutylaluminum hydride in hexanes (Dibal). The resulting mixture was stirred for 6 minutes. The reaction was quenched with MeOH (0.5 ml), and then Rochelles salt solution (5 ml) and allowed to come to room temperature. 10 ml ether were added. The organic layer was separated and the aqueous phase was extracted with ether. Combined ether extracts were dried (Na₂SO₄), and concentrated. 0.55 g of product was obtained.

EXAMPLE 36

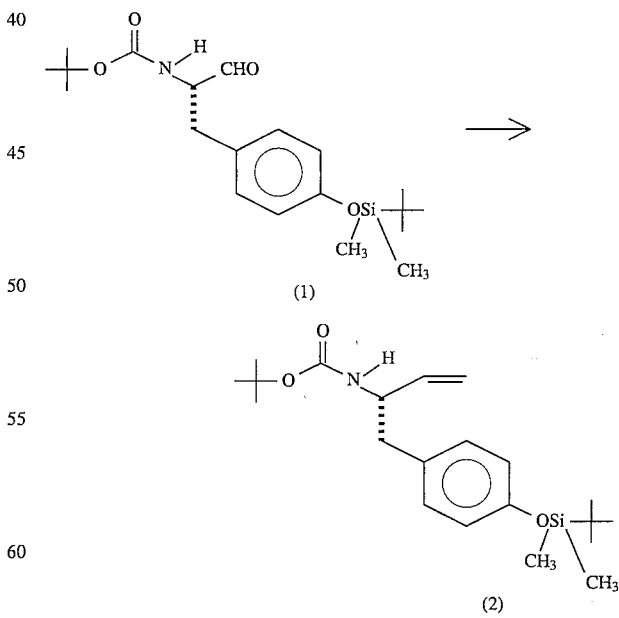

This procedure was run under a nitrogen atmosphere. To a suspension of 1.67 g of methyl triphenyl phosphonium bromide in 10 ml of tetrahydrofuran (THF) was added 2.88 ml of a 1.6N solution of n-BuLi in THF and the yellow-orange colored mixture was stirred at room temperature for one-half hour, cooled to −78° C., and a solution of 0.546 g of aldehyde (1)in THF was added. The reaction mixture was allowed to warm to room temperature, and stirred overnight. tlc (5% EtOAc/hexane) showed a nonpolar product spot. The reaction mixture was partitioned between water and EtOAc. the organic phase, was separated, washed with brine, dried (Na$_2$SO$_4$), and concentrated. The residue was purified by SiO$_2$ column chromatography. 0.23 g of product (2) was obtained.

EXAMPLE 37

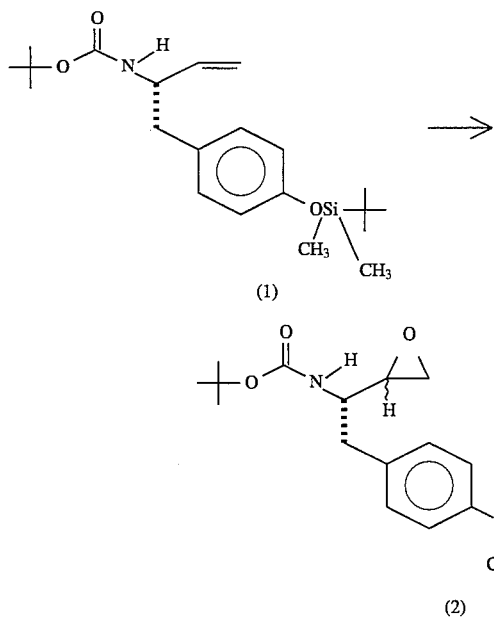

To a solution of 0.546 g of alkene (1) in 5 ml of CHCl$_3$ was added 150 mg of 70% m-chloroperbenzoic acid (m-CPBA) and the mixture was stirred at room temperature for two days.

The reaction mixture was washed with 5% NaHCO$_3$ solution. Dried over Na$_2$SO$_4$, and concentrated. 0.22 g. of product (2) was used without further purification.

EXAMPLE 38

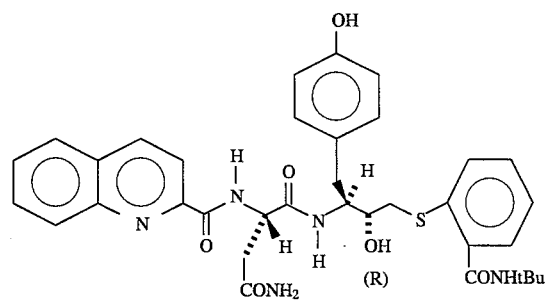

Employing the epoxide from the previous example and following procedures analogous to those described in Examples 4, 5, 6, 26, and 27, the compound (1) was obtained MH$^+$658.5

EXAMPLE 39

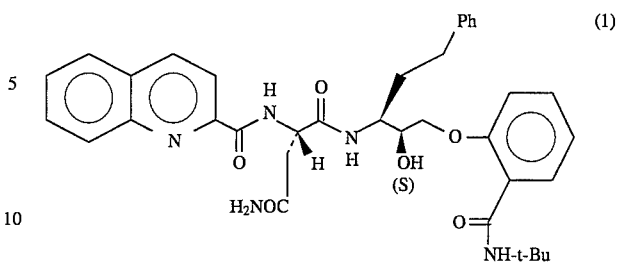

Using hydrocinnamaldehyde,

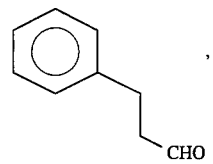

instead of phenylacetaldehyde in example 13 and the procedures set forth in Examples 13, 14, 15, 16, 17, 3, 18, and 27, the compound (1) was obtained.

EXAMPLE 40

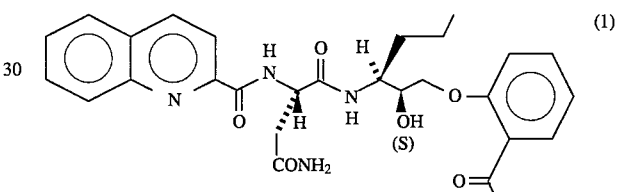

Employing the epoxide

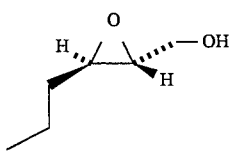

(available from the Aldrich Chemical Company), and following procedures analogous to procedures set forth in Examples 16, 17, 3, 18, and 27, the product (1) was obtained. Measured Mass 578.2989

EXAMPLE 41

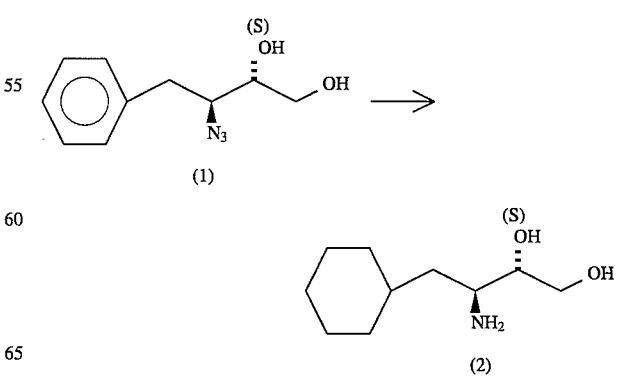

To a mixture of 0.3 g azide and 10 ml of 90% acetic acid was added 0.8 g of 5% Rh/C catalyst, and the azide was subjected to hydrogenation on a pan shaker at 60 psi and 55° C. for 24 hours.

The catalyst was removed by filtration. The filtrate was concentrated under reduced pressure. Traces of acetic acid was removed by azeotroping with toluene. NMR of the crude product showed no aromatic protons. 0.28 g of the product was obtained.

The crude product was used for further reaction without purification.

EXAMPLE 42

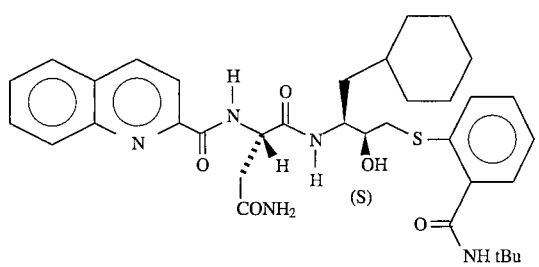
(1)

Using the amine from the previous reaction and procedures analogous to those set forth in Examples 19, 20, 21, 4, 5, 6, 26, and 27, the product (1) was obtained HRFABMS MH+, 648.3233.

What is claimed is:
1. A compound of the formula

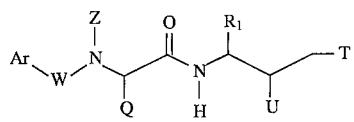

or a pharmaceutically acceptable salt thereof,
wherein Ar is

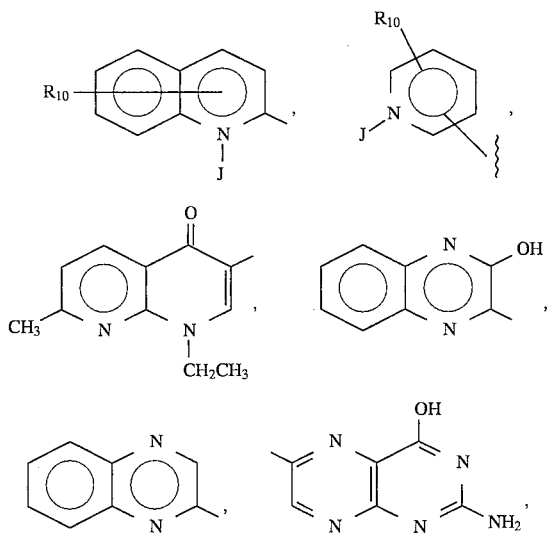

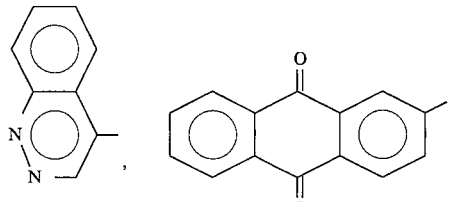

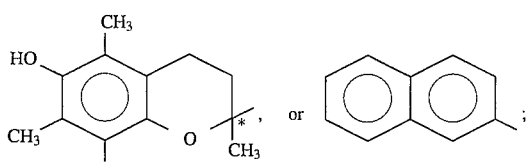

*denotes a mixture of isomers $R_{10}$ is H or OH;

J is O or an electron pair;

W is

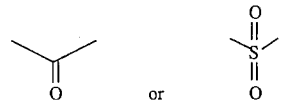

Q is

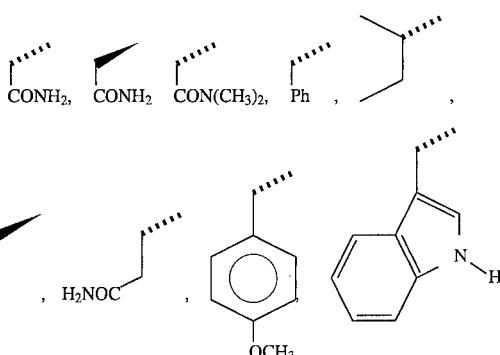

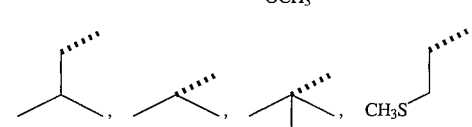

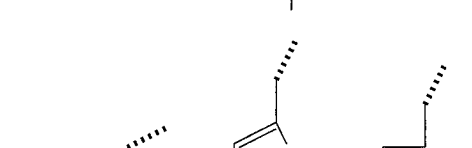

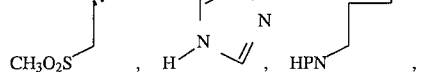

-continued

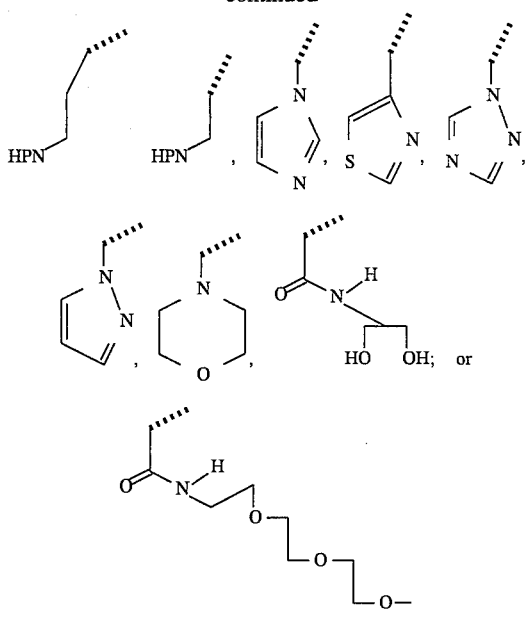

Z is H or Z and Q taken together are —(CH$_2$)$_3$—, or —(CH$_2$)$_4$—;

P is H, CBZ or tBOC;

R$_1$ is

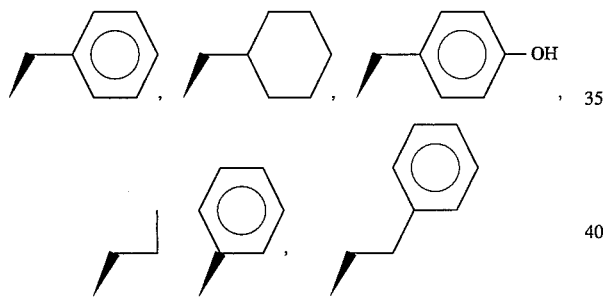

U is

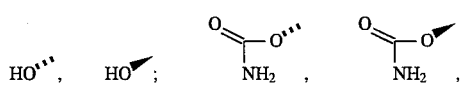

T is —Y—L wherein wherein Y is —SO—, —SO$_2$—, S, or O

L is

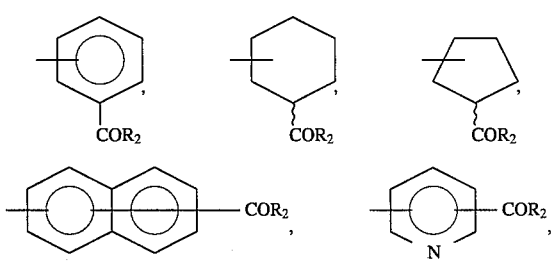

-continued

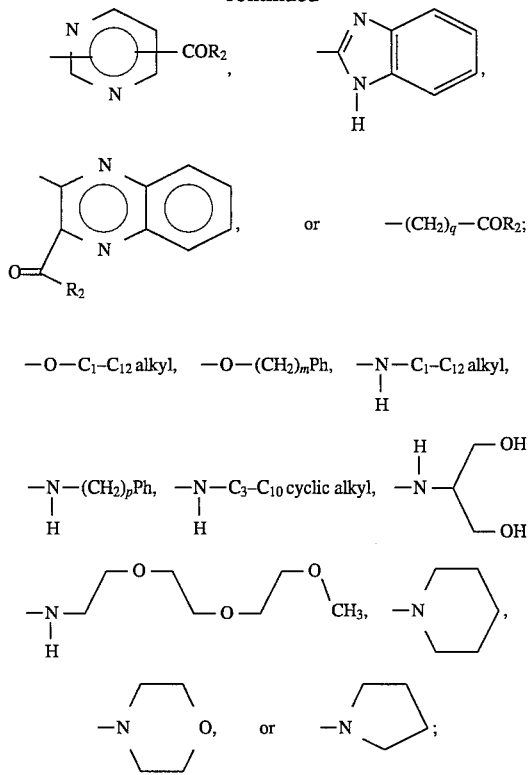

—O—C$_1$-C$_{12}$ alkyl, —O—(CH$_2$)$_m$Ph, —N(H)—C$_1$-C$_{12}$ alkyl,

—N(H)—(CH$_2$)$_p$Ph, —N(H)—C$_3$-C$_{10}$ cyclic alkyl, —N(H)—CH(CH$_2$OH)$_2$

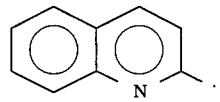

m is 0, 1 or 2;
p is 0, 1, or 2; and
q is 0, 1, or 2; or an isomer thereof.

2. A compound according to claim 1, wherein W is

3. A compound according to claim 1, wherein Z is H.
4. A compound according to claim 1, wherein U is (S) HO.
5. A compound according to claim 1, wherein Ar is

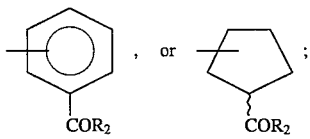

6. A compound according to claim 1, wherein T is —Y—L and Y is S.
7. A compound according to claim 6, wherein L is

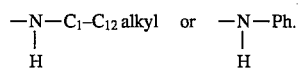

and R$_2$ is

—N(H)—C$_1$-C$_{12}$ alkyl  or  —N(H)—Ph.

8. A compound according to claim 1, wherein R$_2$ is NH tBu or NHPh.

9. A compound according to claim 2 selected from the group consisting of
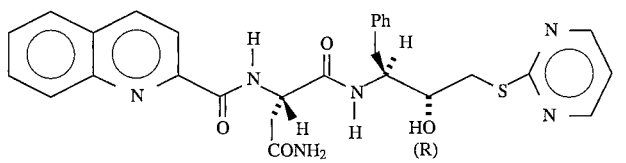
1.
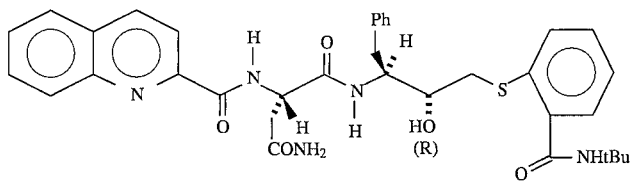
2.
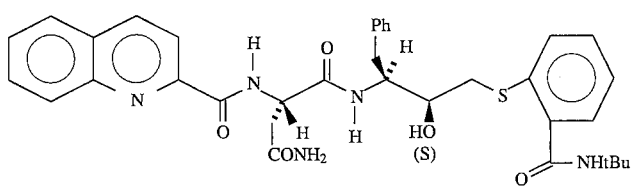
3.
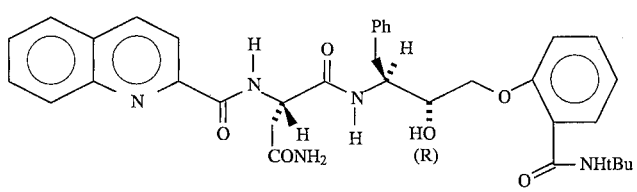
4.
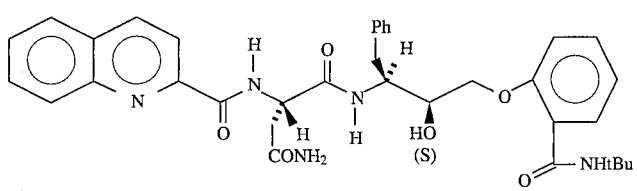
5.
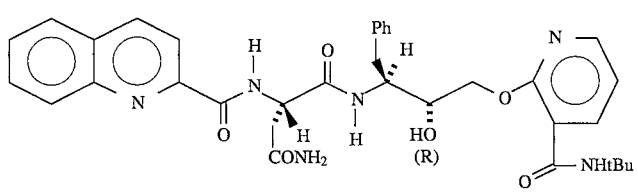
6.
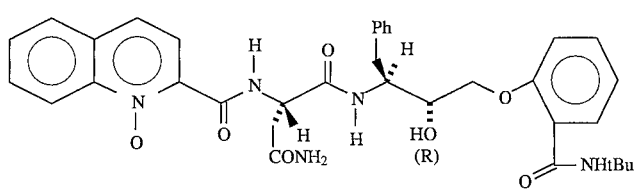
7.
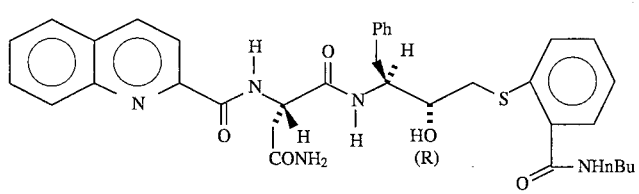
8.

-continued
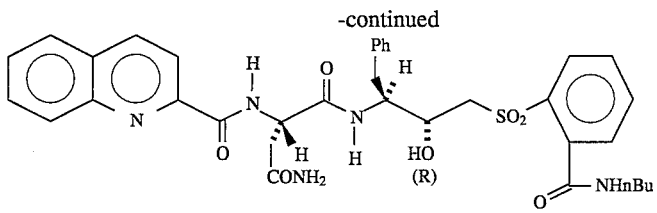
9.
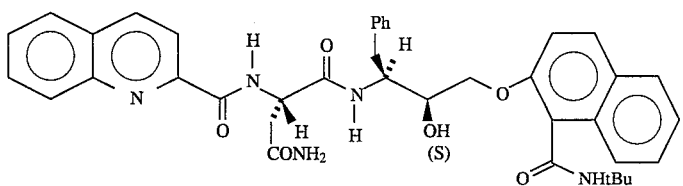
10.
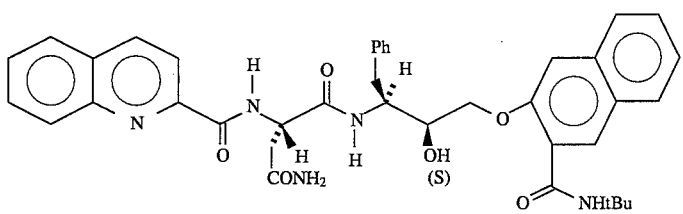
11.
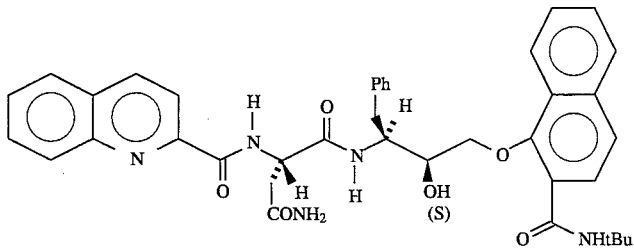
12.
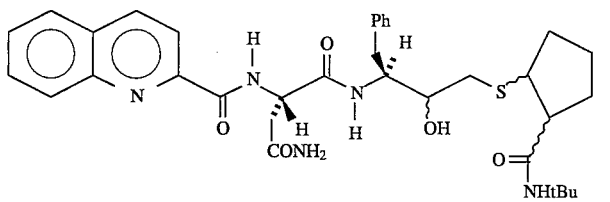
13.
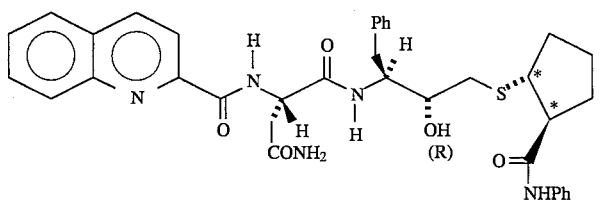
14.
as used here and below, * means that the relative stereochemistry of the two chiral centers is known, but the absolute stereochemistry is not known
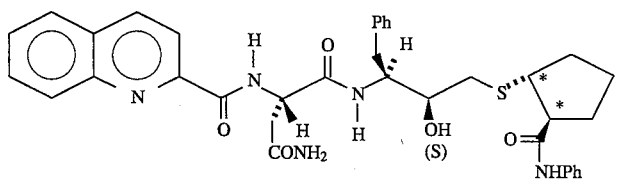
15.

16. 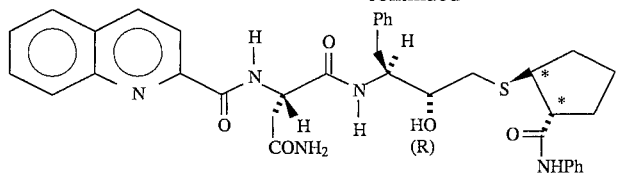
17. 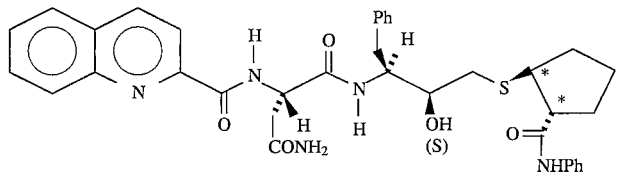
18. 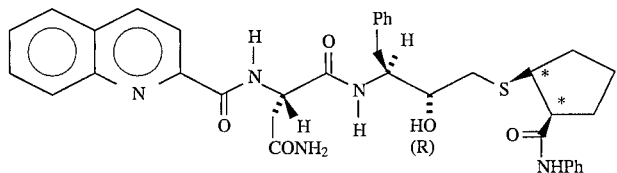
19. 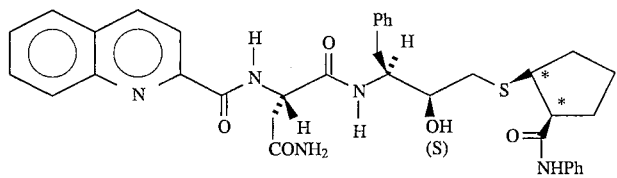
20. 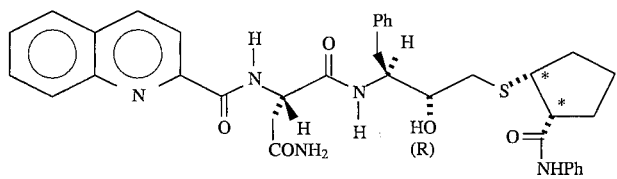
21. 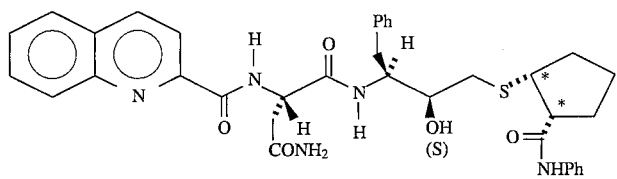
22. 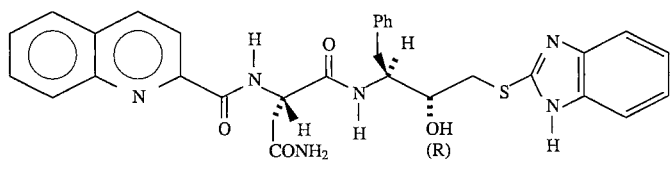
23. 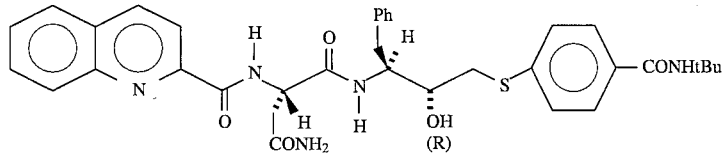
24. 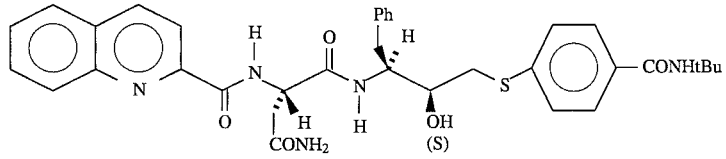

-continued
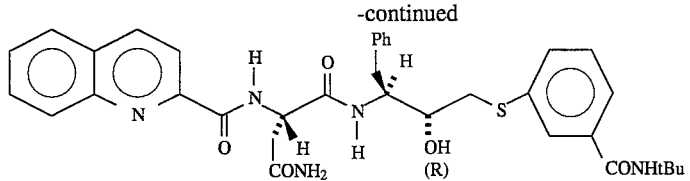 25.
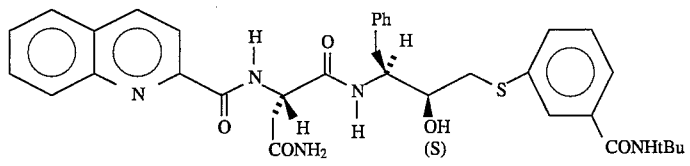 26.
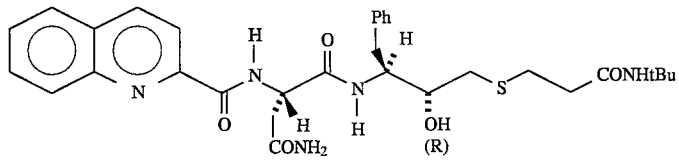 27.
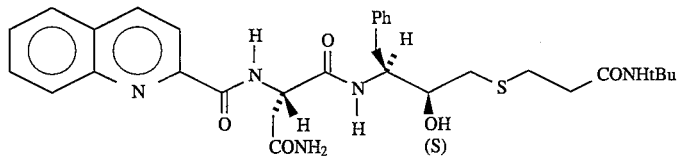 28.
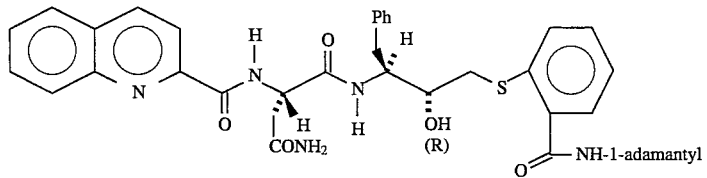 29.
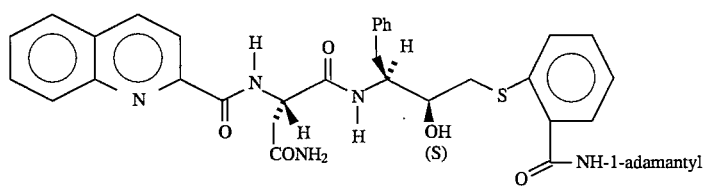 30.
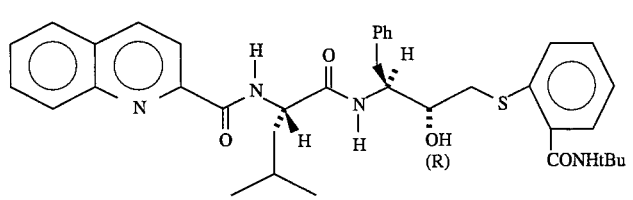 31.
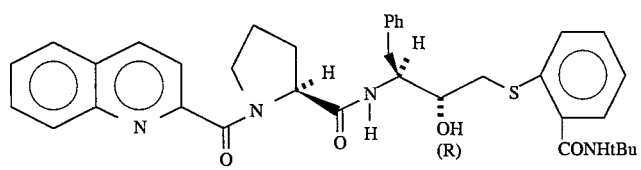 32.
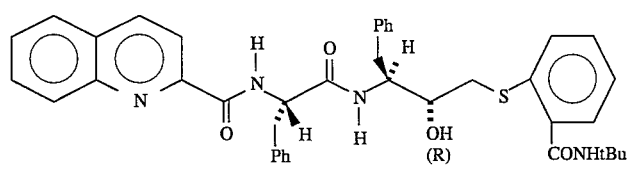 33.

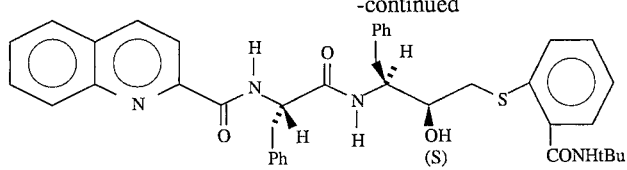
34.
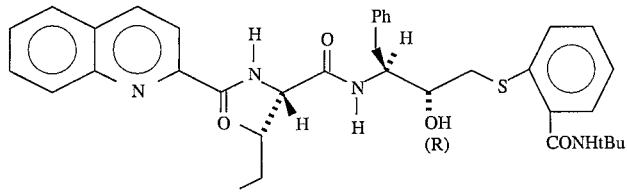
35.
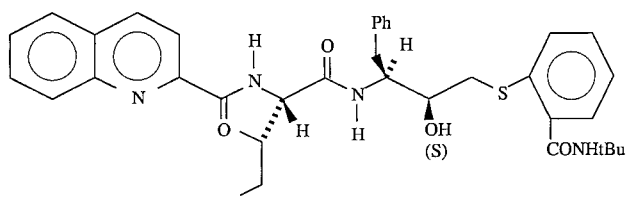
36.
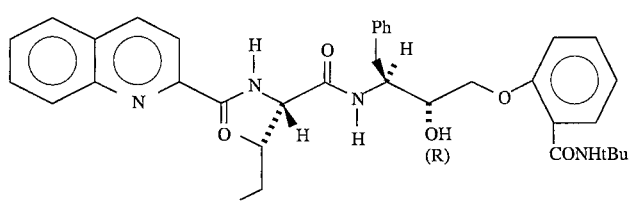
37.
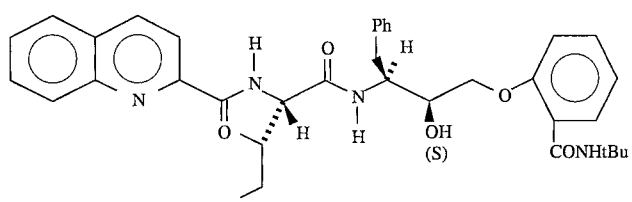
38.
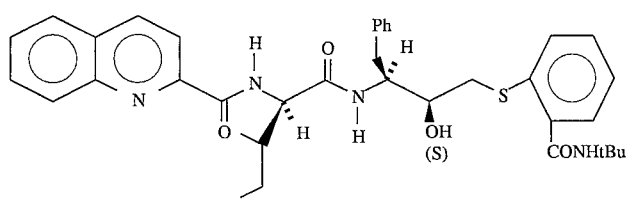
39.
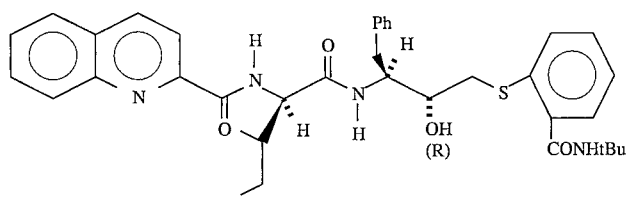
40.
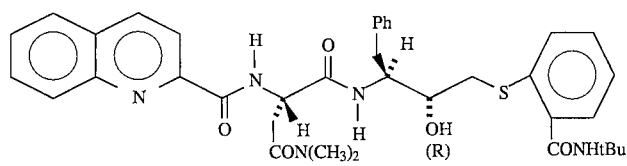
41.

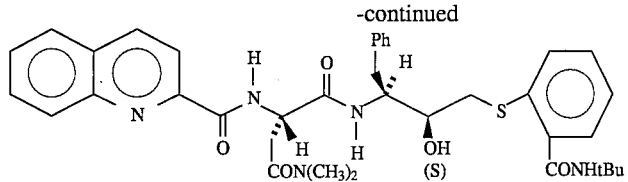
42.
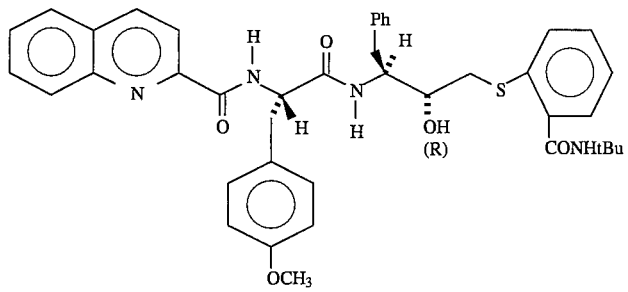
43.
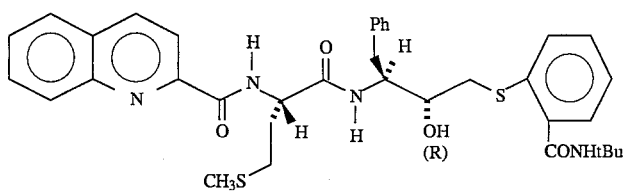
44.
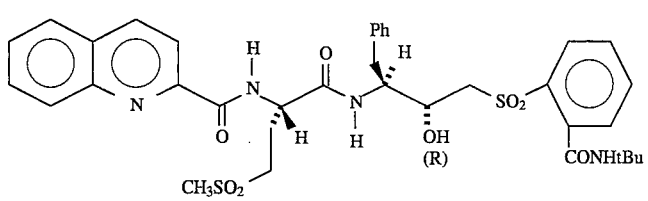
45.
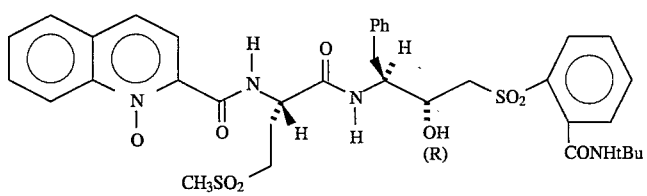
46.
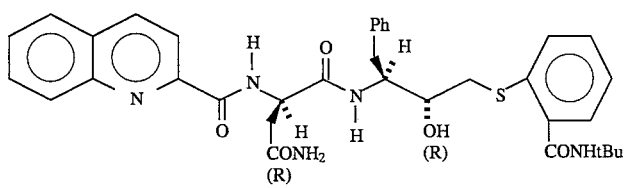
47.
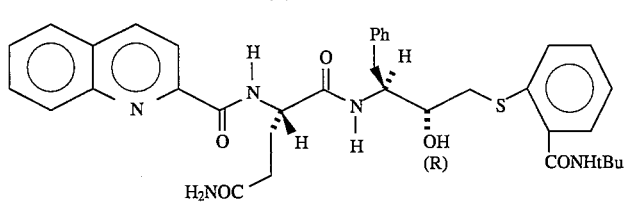
48.
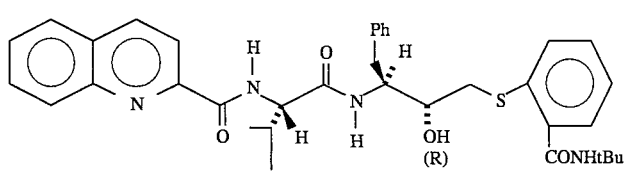
49.

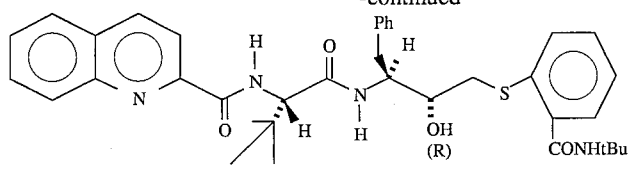
50.
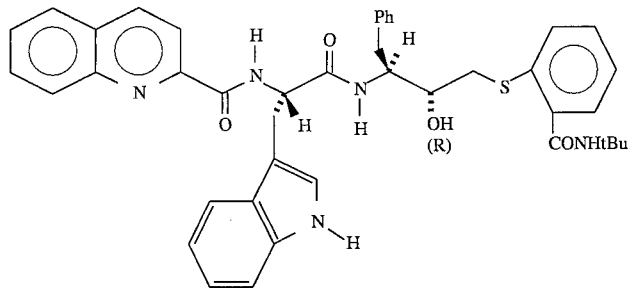
51.
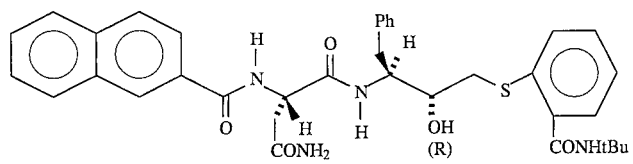
52.
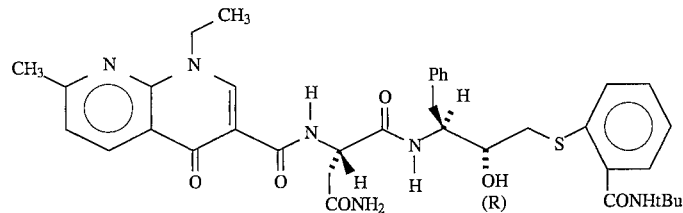
53.
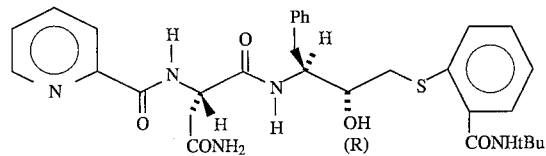
54.
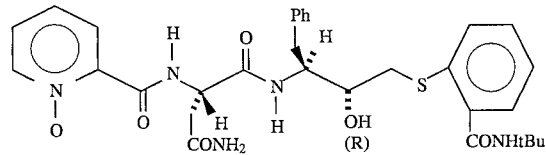
55.
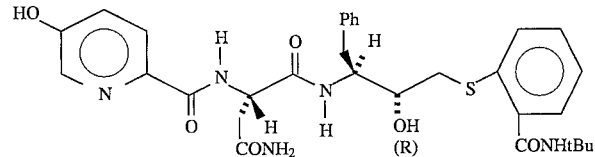
56.
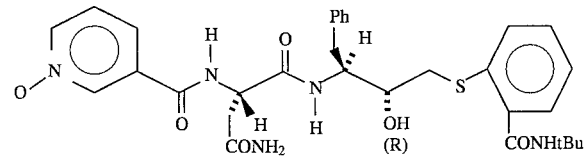
57.
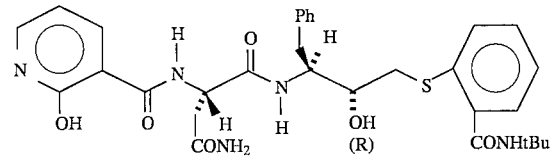
58.

-continued
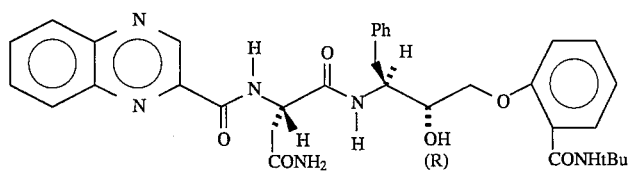 59.
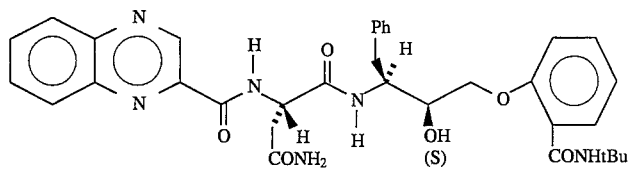 60.
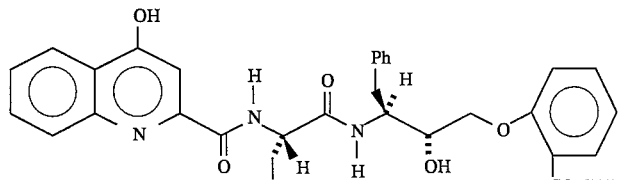 61.
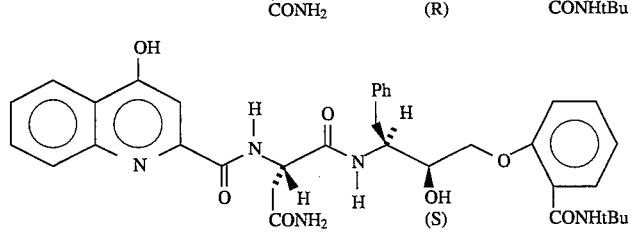 62.
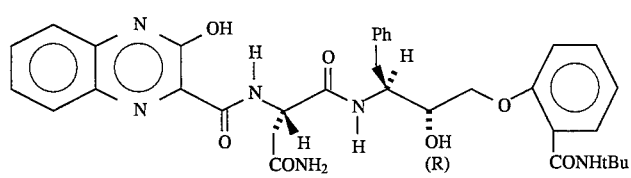 63.
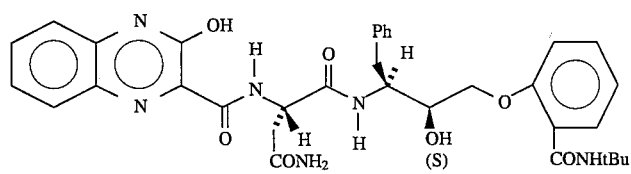 64.
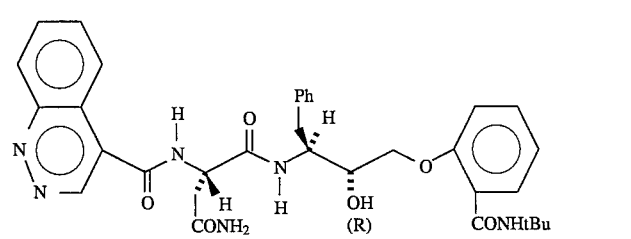 65.
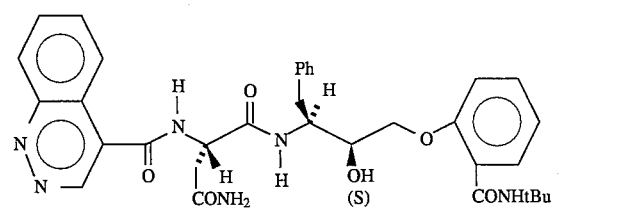 66.

-continued
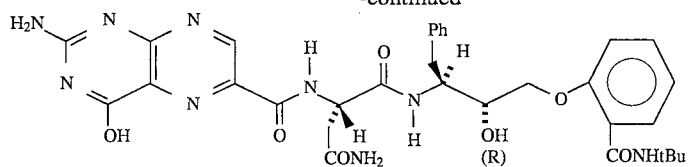
67.
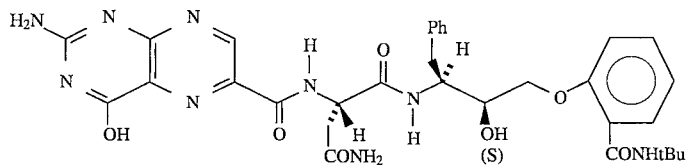
68.
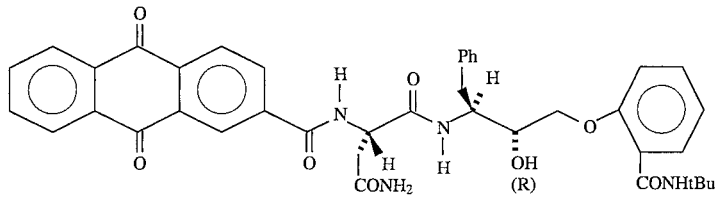
69.
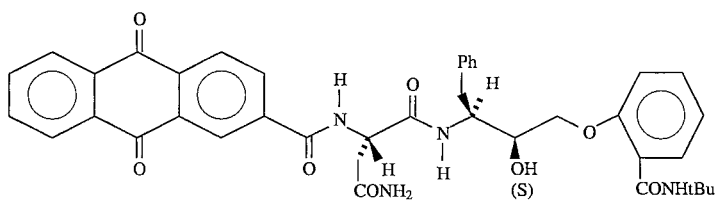
70.
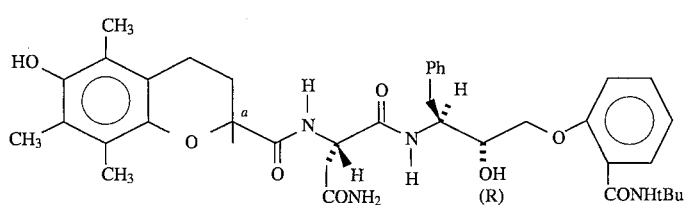
71.
a = a mixture of isomers at this chiral center
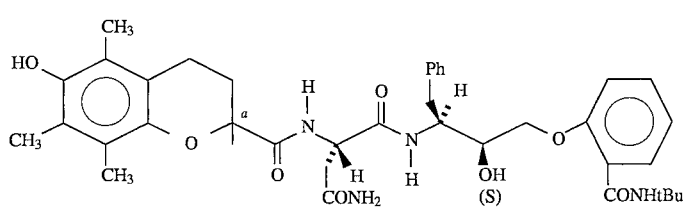
72.
a = a mixture of isomers at this chiral center
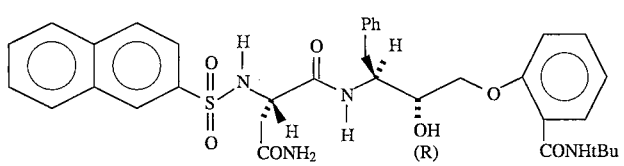
73.
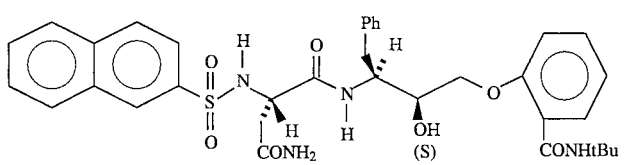
74.

75. 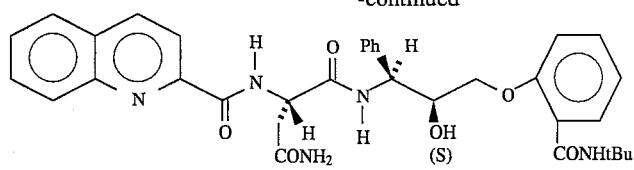
76. 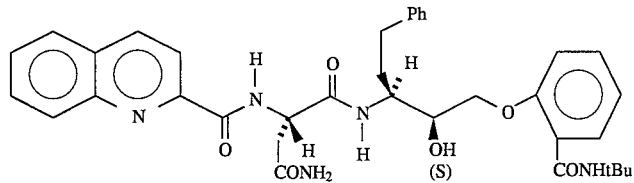
77. 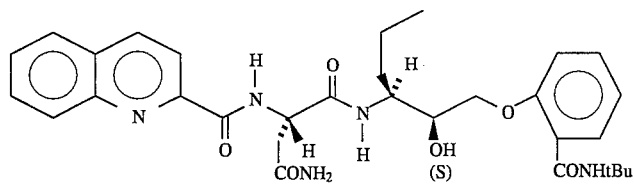
78. 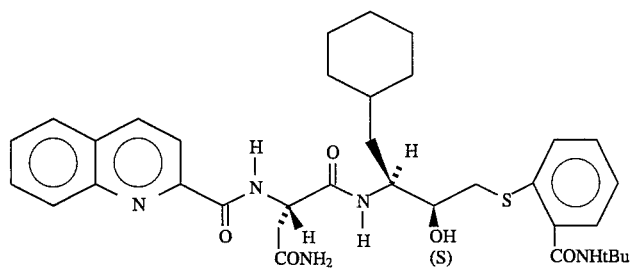
79. 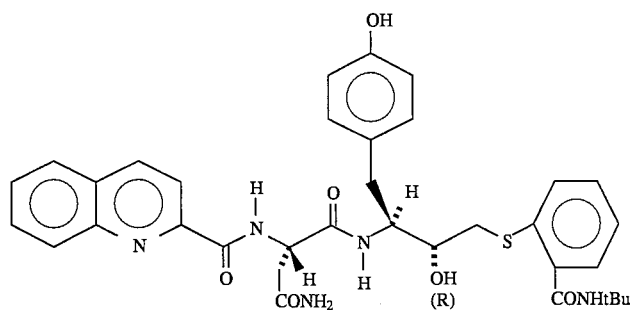
80. 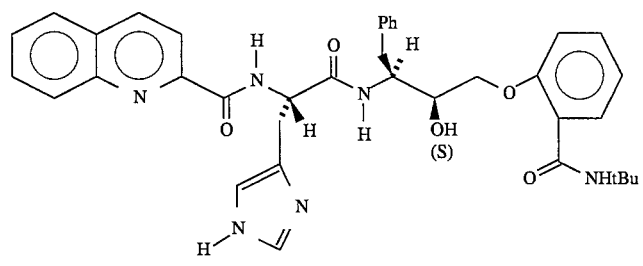
81. 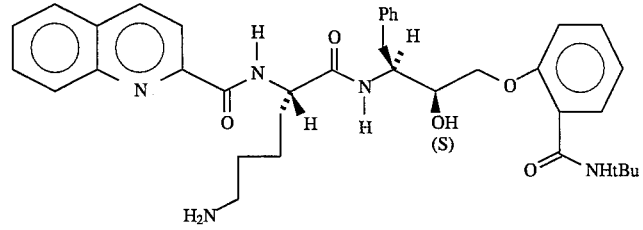

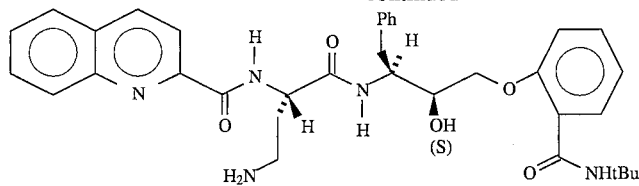
82.
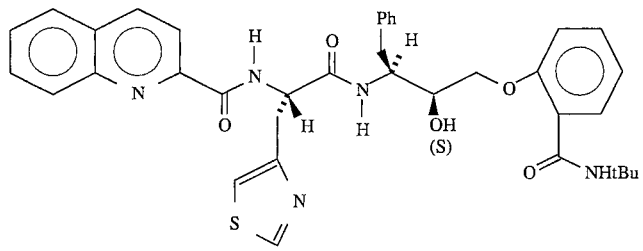
83.
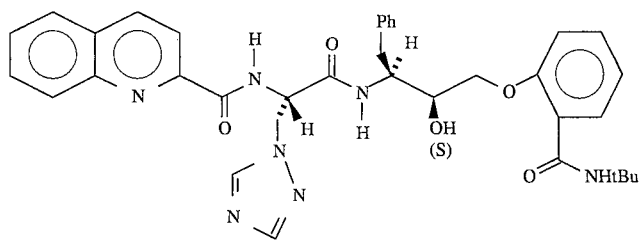
84.
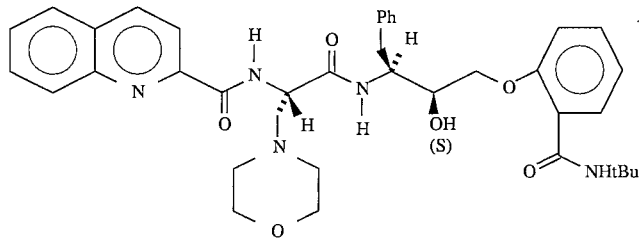
85.
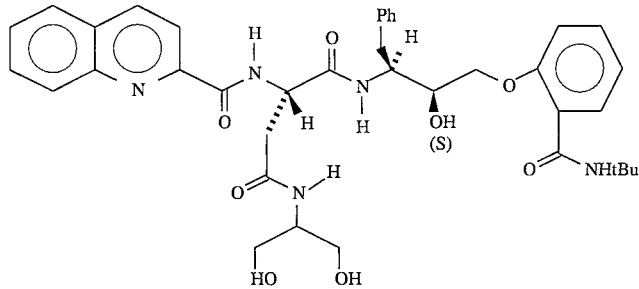
86.
and
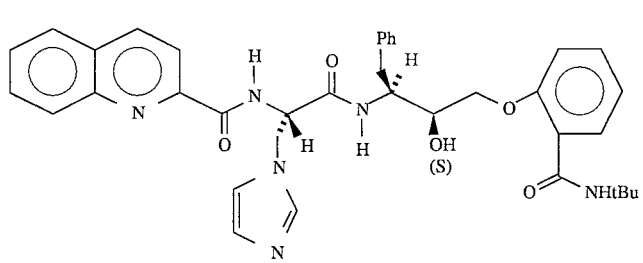
87.
or a pharmaceutically acceptable salt thereof.

10. A compound according to claim 1 selected from the group consisting of

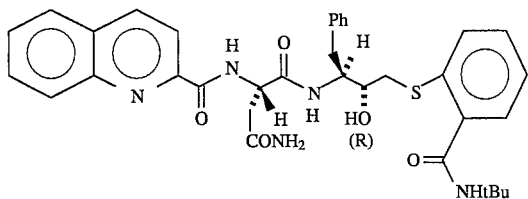

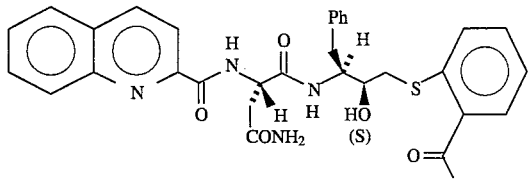

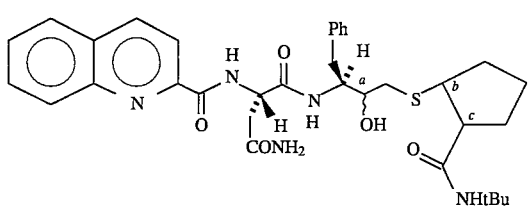

wherein all possible epimers are present at the carbons labelled a, b, and c

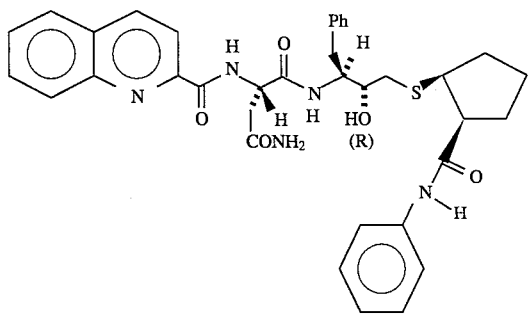

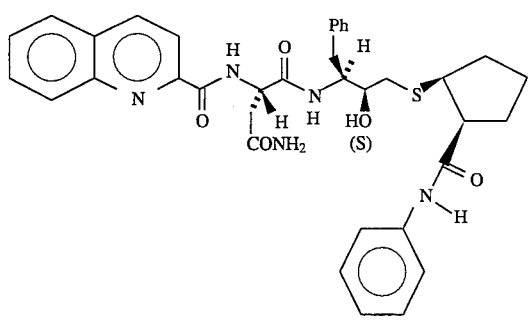

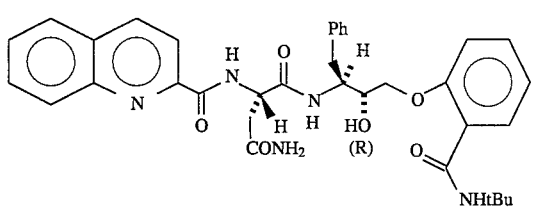

and

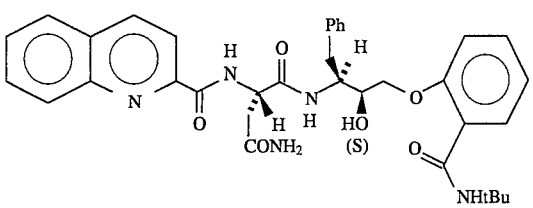

or a pharmaceutically acceptable salt thereof.

11. The compound of according to claim 10,

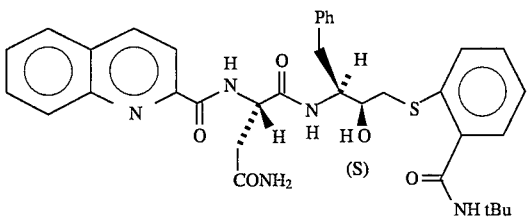

or a pharmaceutically acceptable salt thereof.

12. The compound of according to claim 10,

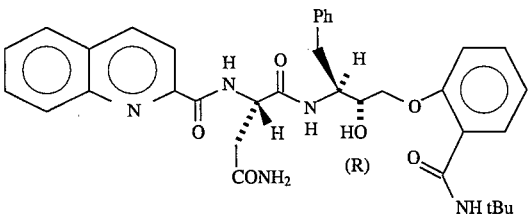

or a pharmaceutically acceptable salt thereof.

13. A compound of the formula

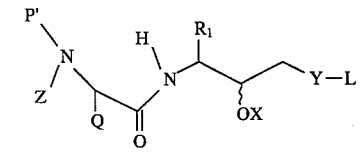

VI wherein P' is t-butoxycarbonyl (BOC) or benzyloxycarbonyl (CBZ), or

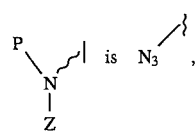

and Q, $R_1$, X, Y, Z and L are as described in claim 1 or a pharmaceutically acceptable salt thereof.

14. A compound of the formula

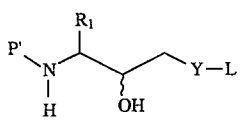

V' wherein P' is t-butoxycarbonyl (BOC) or benzyloxycarbonyl (CBZ), or

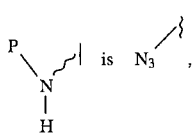

and $R_1$, Y, and L are as described in claim 1, or a pharmaceutically acceptable salt thereof.

15. A compound according to claim 14 of the formula

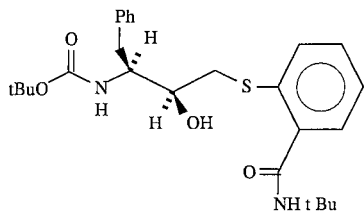

or a pharmaceutically acceptable salt thereof.

16. A compound according to claim 14 of the formula

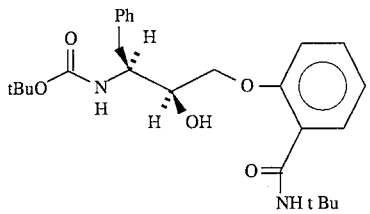

or a pharmaceutically acceptable salt thereof.

17. A pharmaceutical composition comprising a compound according to claim 1, in combination with a pharmaceutically acceptable carrier.

18. A compound according to claim 13 of the formula

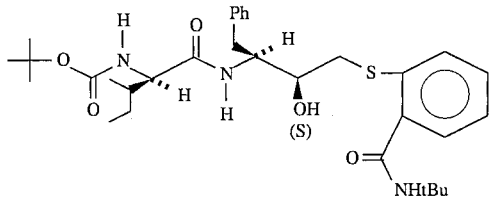

or a pharmaceutically acceptable salt thereof.

* * * * *